United States Patent
Campos et al.

(10) Patent No.: US 9,993,514 B2
(45) Date of Patent: Jun. 12, 2018

(54) COMPOUNDS

(71) Applicant: GlaxoSmithKline Intellectual Property Development Limited, Brentford, Middlesex (GB)

(72) Inventors: Sebastien Andre Campos, Stevenage (GB); John David Harling, Stevenage (GB)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days. days.

(21) Appl. No.: 14/898,832

(22) PCT Filed: Jul. 1, 2014

(86) PCT No.: PCT/EP2014/063901
§ 371 (c)(1),
(2) Date: Dec. 16, 2015

(87) PCT Pub. No.: WO2015/000868
PCT Pub. Date: Jan. 8, 2015

(65) Prior Publication Data
US 2016/0136230 A1    May 19, 2016

(30) Foreign Application Priority Data

Jul. 3, 2013 (GB) .................................. 1311891.4

(51) Int. Cl.
| | |
|---|---|
| *A61K 38/06* | (2006.01) |
| *C07K 5/062* | (2006.01) |
| *C07K 5/065* | (2006.01) |
| *A61K 45/06* | (2006.01) |
| *C07K 5/087* | (2006.01) |

(52) U.S. Cl.
CPC .............. *A61K 38/06* (2013.01); *A61K 45/06* (2013.01); *C07K 5/06017* (2013.01); *C07K 5/06043* (2013.01); *C07K 5/06078* (2013.01); *C07K 5/0812* (2013.01)

(58) Field of Classification Search
CPC ........................... A61K 38/06; C07K 5/06017
See application file for complete search history.

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 4,522,811 A | 6/1985 | Eppstein et al. |
| 5,007,790 A | 4/1991 | Shell |
| 5,169,645 A | 12/1992 | Shukla et al. |
| 5,292,638 A | 3/1994 | Benz et al. |
| 5,492,922 A | 2/1996 | Palkowitz et al. |
| 5,582,837 A | 12/1996 | Shell |
| 5,681,835 A | 10/1997 | Willson |
| 5,681,858 A | 10/1997 | Stevens et al. |
| 5,877,219 A | 3/1999 | Willson |
| 5,972,389 A | 10/1999 | Shell et al. |
| 6,207,716 B1 | 3/2001 | Willson |
| 6,268,391 B1 | 7/2001 | Dickerson et al. |
| 6,303,618 B1 | 10/2001 | Griffin et al. |

(Continued)

FOREIGN PATENT DOCUMENTS

| | | |
|---|---|---|
| CN | 102477033 | 5/2012 |
| EP | 0805147 | 11/1997 |

(Continued)

OTHER PUBLICATIONS

Stoppler, Melissa Conrad. Endometriosis [online], What is Endometriosis? URL http://www.medicinenet.com/endometriosis/article.htm. retreived on Apr. 5, 2017.*

(Continued)

*Primary Examiner* — Shawquia Jackson
(74) *Attorney, Agent, or Firm* — Bryan D. Zerhusen; Locke Lord LLP

(57) ABSTRACT

A compound of formula (I):

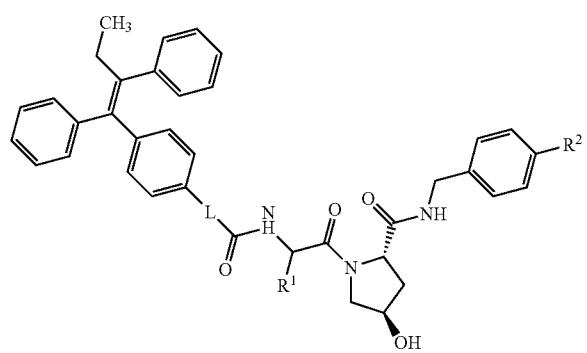

or a pharmaceutically acceptable salt thereof, compositions, combinations and medicaments containing said compounds and processes for their preparation. The invention also relates to the use of said compounds, combinations, compositions and medicaments, for example as inhibitors of the activity of the estrogen receptor, including degrading the estrogen receptor, the treatment of diseases and conditions mediated by the estrogen receptor.

12 Claims, No Drawings

(56) References Cited

U.S. PATENT DOCUMENTS

| | | |
|---|---|---|
| 6,306,663 B1 | 10/2001 | Kenten et al. |
| 6,316,003 B1 | 11/2001 | Frankel et al. |
| 6,323,219 B1 | 11/2001 | Costanzo |
| 6,340,475 B2 | 1/2002 | Shell et al. |
| 6,451,808 B1 | 9/2002 | Cowles |
| 6,488,962 B1 | 12/2002 | Berner et al. |
| 6,559,280 B2 | 5/2003 | Kenten et al. |
| 6,670,348 B1 | 12/2003 | Rosen et al. |
| 7,041,298 B2 | 5/2006 | Deshaies et al. |
| 7,074,620 B2 | 7/2006 | Kenten et al. |
| 7,132,438 B2 | 11/2006 | Frenkel et al. |
| 7,208,157 B2 | 4/2007 | Sakamoto et al. |
| 7,244,851 B2 | 7/2007 | Cohen et al. |
| 7,273,920 B2 | 9/2007 | Kenten et al. |
| 7,294,748 B2 | 11/2007 | Poole et al. |
| 7,345,081 B2 | 3/2008 | Cohen et al. |
| 7,390,784 B2 | 6/2008 | Briesewitz et al. |
| 7,419,975 B2 | 9/2008 | Palermo et al. |
| 7,517,906 B2 | 4/2009 | Condon et al. |
| 7,683,160 B2 | 3/2010 | Eckhardt et al. |
| 7,915,293 B2 | 3/2011 | Ramesh |
| 8,106,191 B2 | 1/2012 | Holt et al. |
| 2002/0051820 A1 | 5/2002 | Shell et al. |
| 2003/0039688 A1 | 2/2003 | Shell et al. |
| 2003/0044466 A1 | 3/2003 | Markey et al. |
| 2003/0104053 A1 | 6/2003 | Gusler et al. |
| 2003/0104062 A1 | 6/2003 | Berner et al. |
| 2003/0133927 A1 | 7/2003 | Defeo-Jones et al. |
| 2003/0147952 A1 | 8/2003 | Lim et al. |
| 2004/0053324 A1 | 3/2004 | Wong et al. |
| 2004/0163138 A1 | 8/2004 | Reed et al. |
| 2004/0114258 A1 | 10/2004 | Wood et al. |
| 2005/0019813 A1 | 1/2005 | Conaway et al. |
| 2005/0215550 A1 | 9/2005 | Tang |
| 2006/0128632 A1 | 6/2006 | Sharma et al. |
| 2006/0149073 A1 | 7/2006 | Tanaka et al. |
| 2006/0258719 A1 | 11/2006 | Combs et al. |
| 2007/0099844 A1 | 5/2007 | Prendergast et al. |
| 2007/0105907 A1 | 5/2007 | Prendergast et al. |
| 2007/0149572 A1 | 6/2007 | Ballentine et al. |
| 2007/0173524 A1 | 7/2007 | Prendergast et al. |
| 2007/0254933 A1 | 11/2007 | Jung et al. |
| 2007/0281907 A1 | 12/2007 | Watkins |
| 2008/0051432 A1 | 2/2008 | Zhang |
| 2008/0108564 A1 | 5/2008 | Holmes et al. |
| 2008/0153837 A1 | 6/2008 | Malilliet et al. |
| 2008/0214501 A1 | 9/2008 | Zhengying et al. |
| 2008/0219929 A1 | 9/2008 | Wischik et al. |
| 2008/0269140 A1 | 10/2008 | Wang et al. |
| 2009/0035362 A1 | 2/2009 | Shih et al. |
| 2009/0054358 A1 | 2/2009 | Small et al. |
| 2009/0298843 A1 | 12/2009 | Kloog et al. |
| 2010/0048517 A1 | 2/2010 | Hu et al. |
| 2010/0056524 A1 | 3/2010 | McIver et al. |
| 2010/0076066 A1 | 3/2010 | Prendergast et al. |
| 2010/0113549 A1* | 5/2010 | Block ............... C07D 207/16 514/397 |
| 2010/0203012 A1 | 8/2010 | Laurent et al. |
| 2011/0195043 A1 | 8/2011 | Sun et al. |
| 2011/0269793 A1 | 11/2011 | Maccioni et al. |
| 2012/0270800 A1 | 10/2012 | Verdine et al. |
| 2013/0274259 A1 | 10/2013 | Zhang et al. |
| 2014/0066625 A1 | 3/2014 | Mautiino et al. |
| 2014/0088143 A1 | 3/2014 | Jain |
| 2014/0161720 A1 | 6/2014 | Garkavtsev et al. |
| 2014/0194404 A1 | 7/2014 | McElroy et al. |
| 2014/0235629 A1 | 8/2014 | Bartberger et al. |
| 2014/0243372 A1 | 8/2014 | Rew |
| 2014/0296243 A1 | 10/2014 | Albrecht et al. |
| 2014/0302523 A1 | 10/2014 | Crews et al. |
| 2014/0329799 A1 | 11/2014 | Seganish et al. |
| 2014/0329800 A1 | 11/2014 | Gao et al. |
| 2014/0356322 A1 | 12/2014 | Crews et al. |
| 2014/0371206 A1 | 12/2014 | Albrecht et al. |
| 2015/0011532 A1 | 1/2015 | Paidi et al. |
| 2015/0045339 A1 | 2/2015 | Takasaki et al. |
| 2015/0045347 A1 | 2/2015 | Dodd et al. |
| 2015/0119421 A1 | 4/2015 | Jain |
| 2015/0119435 A1 | 4/2015 | Crews et al. |
| 2015/0133451 A1 | 5/2015 | Yoshida et al. |
| 2015/0133674 A1 | 5/2015 | Tao et al. |
| 2015/0141402 A1 | 5/2015 | Behenna et al. |
| 2015/0148342 A1 | 5/2015 | Combs et al. |
| 2015/0191464 A1 | 7/2015 | Santella et al. |
| 2015/0256700 A1 | 9/2015 | Sakai |
| 2015/0259288 A1 | 9/2015 | Nam et al. |
| 2015/0274708 A1 | 10/2015 | Seganish et al. |
| 2015/0284405 A1 | 10/2015 | Trzupek et al. |
| 2015/0291562 A1 | 10/2015 | Crew et al. |
| 2015/0344473 A1 | 10/2015 | Du et al. |
| 2015/0329525 A1 | 11/2015 | Crosignani et al. |
| 2015/0352206 A1 | 12/2015 | Gajewski et al. |
| 2016/0002265 A1 | 1/2016 | Jenkins et al. |
| 2016/0022619 A1 | 1/2016 | Balog et al. |
| 2016/0045607 A1 | 2/2016 | Crew et al. |
| 2016/0058872 A1 | 3/2016 | Crew et al. |
| 2016/0075711 A1 | 3/2016 | Sherer |
| 2016/0083375 A1 | 3/2016 | Paidi et al. |
| 2016/0137595 A1 | 5/2016 | Markwalder et al. |
| 2016/0137652 A1 | 5/2016 | Beck et al. |
| 2016/0137653 A1 | 5/2016 | Beck et al. |
| 2016/0143870 A1 | 5/2016 | Markwalder et al. |
| 2016/0168152 A1 | 6/2016 | Li et al. |
| 2016/0176864 A1 | 6/2016 | Norris et al. |
| 2016/0200674 A1 | 7/2016 | Markwalder et al. |
| 2016/0214972 A1 | 7/2016 | Jin et al. |
| 2016/0272639 A1 | 9/2016 | Crew et al. |
| 2016/0297822 A1 | 10/2016 | Yang et al. |
| 2016/0303109 A1 | 10/2016 | Jain |
| 2016/0326151 A1 | 11/2016 | Gummadi et al. |
| 2016/0333009 A1 | 11/2016 | Bartlett et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0204093 A1 | 7/2017 | Chan et al. |
| 2017/0209446 A1 | 7/2017 | Altman et al. |
| 2017/0217981 A1 | 8/2017 | Altman et al. |
| 2017/0247388 A1 | 8/2017 | Altman et al. |
| 2017/0275297 A1 | 9/2017 | Altman et al. |

FOREIGN PATENT DOCUMENTS

| | | |
|---|---|---|
| WO | WO 1990/011757 | 10/1990 |
| WO | WO 1993/018755 | 9/1993 |
| WO | WO 1997/030034 | 8/1997 |
| WO | WO 1997/042216 | 11/1997 |
| WO | WO 1997/047285 | 12/1997 |
| WO | WO 1998/011879 | 3/1998 |
| WO | WO 1998/018493 | 5/1998 |
| WO | WO 1998/045287 | 10/1998 |
| WO | WO 1998/055107 | 12/1998 |
| WO | WO 1999/002175 | 1/1999 |
| WO | WO 1999/013077 | 3/1999 |
| WO | WO 2000/022110 | 4/2000 |
| WO | WO 2000/050445 | 8/2000 |
| WO | WO 2000/066119 | 11/2000 |
| WO | WO 2001/028593 | 4/2001 |
| WO | WO 2001/032217 | 5/2001 |
| WO | WO 2001/056544 | 8/2001 |
| WO | WO 2001/075145 | 10/2001 |
| WO | WO 2001/097783 | 12/2001 |
| WO | WO 2002/022577 | 3/2002 |
| WO | WO 2002/032416 | 4/2002 |
| WO | WO 2002/066512 | 8/2002 |
| WO | WO 2002/076986 | 10/2002 |
| WO | WO 2002/080926 | 10/2002 |
| WO | WO 2002/096404 | 12/2002 |
| WO | WO 2002/100845 | 12/2002 |
| WO | WO 2003/013541 | 2/2003 |
| WO | WO 2003/035029 | 5/2003 |
| WO | WO 2003/035039 | 5/2003 |
| WO | WO 2003/035040 | 5/2003 |
| WO | WO 2003/035041 | 5/2003 |
| WO | WO 2003/035177 | 5/2003 |

(56) References Cited

FOREIGN PATENT DOCUMENTS

| | | |
|---|---|---|
| WO | WO 2003/057820 | 7/2003 |
| WO | WO 2004/100868 | 11/2004 |
| WO | WO 2005/118588 | 12/2005 |
| WO | WO 2006/069063 | 6/2006 |
| WO | WO 2006/113942 | 10/2006 |
| WO | WO 2007/022638 | 3/2007 |
| WO | WO 2007/101347 | 9/2007 |
| WO | WO 2007/106670 | 9/2007 |
| WO | WO 2007/125405 | 11/2007 |
| WO | WO 2007/129195 | 11/2007 |
| WO | WO 2007/130626 | 11/2007 |
| WO | WO 2008/011392 | 1/2008 |
| WO | WO 2008/014236 | 1/2008 |
| WO | WO 2008/067495 | 6/2008 |
| WO | WO 2008/109727 | 9/2008 |
| WO | WO 2008/109731 | 9/2008 |
| WO | WO 2008/115663 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/005510 | 1/2011 |
| WO | WO 2011/008260 | 1/2011 |
| WO | WO 2011/043371 | 4/2011 |
| WO | WO 2011/082007 | 7/2011 |
| WO | WO 2011/119565 | 9/2011 |
| WO | WO 2011/143660 | 11/2011 |
| WO | WO 2011/143669 | 11/2011 |
| WO | WO 2011/160016 | 12/2011 |
| WO | WO 2012/003281 | 1/2012 |
| WO | WO 2012/007375 | 1/2012 |
| WO | WO 2012/009649 | 1/2012 |
| WO | WO 2012/040527 | 3/2012 |
| WO | WO 2012/054110 | 4/2012 |
| WO | WO 2012/061299 | 5/2012 |
| WO | WO 2012/078559 | 6/2012 |
| WO | WO 2012/090104 | 7/2012 |
| WO | WO 2012/142498 | 10/2012 |
| WO | WO 2013/042137 | 3/2013 |
| WO | WO 2013/071035 | 5/2013 |
| WO | WO 2013/071039 | 5/2013 |
| WO | WO 2013/106535 | 7/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/058691 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000867 | 1/2015 |
| WO | WO 2015/000868 | 1/2015 |
| WO | WO 2015/006524 | 1/2015 |
| WO | WO 2015/011084 | 1/2015 |
| WO | WO 2015/022332 | 2/2015 |
| WO | WO 2015/015318 | 5/2015 |
| WO | WO 2015/067770 | 5/2015 |
| WO | WO 2015/074064 | 5/2015 |
| WO | WO 2015/104688 | 7/2015 |
| WO | WO 2015/175632 | 11/2015 |
| WO | WO 2016/011390 | 1/2016 |
| WO | WO 2016/138114 | 1/2016 |
| WO | WO 2016/053769 | 4/2016 |
| WO | WO 2016/053770 | 4/2016 |
| WO | WO 2016/053771 | 4/2016 |
| WO | WO 2016/053772 | 4/2016 |
| WO | WO 2016/144844 | 9/2016 |
| WO | WO 2016/144846 | 9/2016 |
| WO | WO 2016/144847 | 9/2016 |
| WO | WO 2016/144848 | 9/2016 |
| WO | WO 2016/144849 | 9/2016 |
| WO | WO 2016/146985 | 9/2016 |
| WO | WO 2017/011590 | 1/2017 |
| WO | WO 2017/030814 | 2/2017 |

OTHER PUBLICATIONS

Stoppler, Melissa Conrad. Endometriosis [online], What is What about surgery for endometriosis? URL http://www.medicinenet.com/endometriosis/article.htm. retrieved on Apr. 5, 2017.*
Cyrus, K., et al. "Jostling for position: optimizing linker location in the design of estrogen receptor-targeting PROTACs." Chemmedchem, Jul. 5, 2010, vol. 5, No. 7, pp. 979-985.
Burke, P.J., et al. "Design, Synthesis, and Biological Evaluation of Doxorubicin-Formaldehyde Conjugates Targeted to Breast Cancer Cells." Journal of Medicinal Chemistry, Jan. 24, 2004, vol. 47, No. 5, pp. 1193-1206.
Willson, T.M., et al. "3o-[4-(1,2-Diphenylbut-1-Enyl)Phenyl] Acrylic Acid: A Non-Steroidal Estrogen With Functional Selectivity for Bone Over Uterus in Rats." Journal of Medicinal Chemistry, American Chemical Society, US, May 25, 1994, vol. 37, No. 11, pp. 1550-1552.
Abella, J.V., et at., (2005). "Met/Hepatocyte Growth Factor Receptor Ubiquitination Suppresses Transformation and Is Required for Hrs Phosphorylation", Mol Cell Biol 25, 9632-9645.
Abraham, R.T., "Phosphatidylinositol 3-kinase related kinases", (1996), Current Opinion in Immunology. 8(3) 412-418.
Agashe, V. R., et al., "Initial hydrophobic collapse in the folding of barstar", Nature 377, 754-757, doi:10.1038/377754a0 (1995).
Aghajanyy, Mariam et al., "Chemical genetics of TOR identified an SCF family E3 ubiquitin ligase inhibitor", Nature Biotechnology, Jul. 27, 2010, 28(7):738-542.
Ahn, et al., "HIF-lalpha peptide derivatives with modifications at the hydroxyproline residue as activators of HIF-lalpha", Bioorg Med Chem Lett. 19(15), 2009, 4403-4405.
Albrecht, B., et al., "Identification of a benzoisoxazoloazepine inhibitor (CPI-0610) of the bromodomain and extra-terminal (BETA) family as a candidate for human clinical trials", Journal Med. Chem. 59, 1330-1339 (2016).
Allan, GF, et. al, "Therapeutic androgen receptor ligands", Nuclear Receptor Signaling, 2003, 1, e009 DOI:10.621.01009 9 1-4.
Anido, J., et al., "ZD1839, a Specific Epidermal Growth Factor Receptor (EGFR) Tyrosine Kinase Inhibitor, Induces the Formation of Inactive EGFR/HER2 and EGFR/HER3 Heterodimers and Prevents Heregulin Signaling in HER2-overexpressing Breast Cancer Cells", Clinical Cancer Research 9, 1274-1283 (2003).
Ardecky, RJ, et al., "Design, synthesis and evaluation of inhibitor of apoptosis protein (IAP) antagonists that are highly selective for the BIR2 domain of XIAP", Bioorg. Med. Chem., 23(14):4253-4257 (2013).
Ariza, M. et al, "Tau positron emission tomography (PET) imaging: past, present, and future", in Journal of Medicinal Chemistry 2015, 58, 4365-4382.
Asangani, I.A. et al., "Therapeutic Targeting of BET Bromodomain Proteins in Castration-Resistant Prostate Cancer", Nature, 2014, 510: 278-282.
Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).
Asaoka, Y., et al., "Gastric cancer cell line Hs746T harbors a splice site mutation of c-Met causing juxtamembrane domain deletion", Biochem Biophys Res Commun 394, 1042-1046 (2010).

(56) References Cited

OTHER PUBLICATIONS

Ashby, M.N. (1998), "CaaX converting enzymes", Current Opinion in Lipidology. 9 (2) 99-102.
Banaszynski, L. A. et al. "A Rapid, Reversible, and Tunable Method to Regulate Protein Function in Living Cells Using Synthetic Small Molecules", Cell. vol. 126: 995-1004. Sep. 8, 2006.
Banaszynski, L. A. et al., "Chemical control of protein stability and function in living mice", Nature Medicine. vol. 14(10): 1123-1127, Oct. 2008.
Baratta, M.G. et al., "An in-tumor genetic screen reveals that the BET bromodomain protein, BRD4, is a potential therapeutic target in ovarian carcinonoma", PNAS, 112: 232-237 (2015).
Bargagna-Mohan, et al., "Use of PROTACS as molecular probes of angiogenesis", Bioorg Med Chem Left. 15(11) 2005, 2724-2727.
Barker, A.J. et al., "Studies Leading to the Identification of ZD1839 (IressaTM): An Orally Active, Selective Epidermal Growth Factor Receptor Tyrosine Kinase Inhibitor Targeted to the Treatment of Cancer", Bioorganic and Medicinal Chemistry Letters 2001, 11(14), 1911-1914.
Beck, S. et al., "Fluorophore-assisted light inactivation: a high-throughput tool for direct target validation of proteins", Proteomics, vol. 2, pp. 247-255 (2002).
Belkina, A.C. et al., "BET domain co-regulators in obesity, inflammation and cancer", Nat. Rev. Cancer, 12 (2012) 465-477.
Belshaw, P.C., et al., "Controlling protein association and subcellular localization with a synthetic ligand that induces heterodimerization of proteins", Proc. Natl. Acad. Sci. USA 93:4604-4607 (1996).
Berge, et al, "Pharmaceutical Salts", J. Pharm. Sci. 1977, 66, 1-19.
Birchmeier, C., et al., "Met, metastasis, motility and more", Nat Rev Mol Cell Biol 4, 915-925 (2003).
Blond-Elguindi, S. et al., "Affinity panning of a library of peptides displayed on bacteriophages reveals the binding specificity of BiP", Cell 75, 717-728, doi:0092-8674(93)90492-9 [pii] (1993).
Boi, M. et al., "The BET Bromodomain inhibitor OTX015 Affects pathogenetic Pathways in Preclinical B-cell Tumor Models and synergizes with Targeted Drugs", Clin. Cancer Res., (2015) 21(7):1628-1638.
Boitano, et al., "Aryl Hydrocarbon Receptor Antagonists Promote the Expansion of Human Hematopoietic Stem Cells", Science Sep. 10, 2010: vol. 329, pp. 1345-1348.
Bolen, et al., "Leukocyte protein tyrosine kinases: potential targets for drug discovery", Annual review of Immunology. 15:371-404 (1997).
Bondeson, et al., "Catalytic in vivo protein knockdown by small-molecule PROTACS", National Chem Biol. 11(8) Aug. 2015, 611-617.
Borchardt, A., et al., "Small Molecule-dependent genetic selection in stochastic nanodroplets as a means of detecting protein-ligand interactions on a large scale", Chem. Bio., 4:961-968 (1997).
Bos, J. L., "ras oncogenes in human cancer: a review", Cancer Res 49, 4682-4689 (1989).
Bradbury, RH, et. al, "Small-molecule androgen receptor downregulators as an approach to treatment of advanced prostate cancer", Bioorganic & Medicinal Chemistry Letters, 2011, 21:5442-5445.
Braun, et al., "Quantitative analysis of bifunctional molecules", Biochemistry, vol. 43, pp. 2004, 5406-5407.
Brekken, R.A. et al., "Selective Inhibition of VEGFR2 Activity by a monoclonal Anti-VEGF antibody blocks tumor growth in mice", Cancer Res. (2000) 60, 5117-5124.
Briscoe, C. P. et al., "The orphan G protein-coupled receptor GPR40 is activated by medium and long chain fatty acids", *J Biol Chem* 278, 11303-11311, doi:10.1074/jbc.M211495200 M211495200 [pii] (2003).
Brodt, et al., "Inhibition of the type I insulin-like growth factor receptor expression and signaling: novel strategies for antimetastatic therapy", (2000), Biochemical Pharmacology, 60. 1101-1107.

Brough, et al., "4,5-Diarylisoxazole HSP90 Chaperone Inhibitors: Potential Therapeutic Agents for the Treatment of Cancer", J Med Chem. 51(2), Jan. 24, 2008, 196-218.
Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and HIF1a", Angew Chem Int Ed Engl.51(46), Oct. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10):4465-4468.
Burke, et al., "Design, Synthesis and Biological Evaluation of Doxorubicin-Formaldehyde Conjugates Targeted to Breast Cancer Cells", Journal of Medicinal Chemistry, Jan. 24, 2004, vol. 47, No. 5, pp. 1193-1206.
Calloway, N.T., et al., "Optimized Fluorescent Trimethoprim Derivatives for in Vivo Protein Labeling", ChemBioChem, 8:767-774 (2007).
Canman, C.E., Lim, D.S. "The role of ATM in DNA damage responses and cancer", (1998), Oncogene 17(25)3301-3308.
Capitosti, S., et al., "Thalidomide analogues demonstrate dual inhibition of both angiogenesis and prostate cancer", Bioorganic & Medicinal Chemistry 12, (2004) 327-336.
Carlson, et al., "Selection of small-molecule mediators of the RNA regulation of PKR, the RNA-dependent protein cinase", Chembiochem 3(9), 2002, 859-865.
Carmony, KC, et al., "Protac-Induced Proteolytic Targeting", Methods Mol. Biol., 2012, vol. 832, pp. 627-638.
CAS 155180-53-3 published 1994.
CAS 186040-53-9 published 1997.
CAS 186798-71-0 published 1997.
CAS 186798-85-6 published 1997.
CAS 534612-78-7 published 2003.
CAS Registry No. 1004933-70-3, which entered STN on Feb. 21, 2008.
CAS Registry No. 871986-52-6 entered STN Jan 16, 2006.
Ceribelli, M. et al., "Blockade of oncongenic IKB kinase activity in diffuse large B-cell lymphoma by bromodomain and extraterminal domain protein inhibitors", PNAS, 111 (2014) 11365-11370.
Chang, et al., "Structural basis for G9a-like protein lysine methyltransferase inhibition by BIX-01294", Nat Struct Mol Biol. 16(3), Mar. 2009, 312-317.
Chapuy, B. et al., "Discovery and characterization of super-enhancer-associated dependencies in diffuse large B cell lymphoma", Cancer Cell, 24 (2013) 777-790.
CHEMBL256713, PubChem (2009); National Center for Biotechnology Information. PubChem Compound Database; CID-44449334, https://pubchem.ncbi.nlm.nih.gov/compound/44449334.
Chemexper.Com (Marco Engeler): "Anthracene," 2016, XP055272008, Retrieved from the Internet on May 12, 2016: URL: http://www.chemexper.com/searchResult.shtml7format=ccd2013%2Cccd&target=structure&options=brandqtyoffercrm&searchValue=120127&tsearchTemplate=rn.value%3D%22%3F%22&Search=Search.
Chemexper.Com Catalog pages: "Fluorescein sodium 518-47-8 Catalog of Chemical Suppliers," XP055272421, Retrieved from the internet on May 12, 2016: URL: https://www.chemexper.comichemicals/supplier/cas/518-47-8+Fluorescein+sodium.html.
Chene, P., et al., "Inhibiting the p53-MDM2 interaction: an important target for cancer therapy" Nat. Rev. Cancer (2003), 3, 102-109.
Chou, et al., "Quantitative analysis of dose-effect relationships: the combined effects of multiple drugs or enzyme inhibitors", 1984, Adv. Enzyme Regul. 22: 27-55.
Chung, et al., "Discovery and Characterization of Small Molecule Inhibitors of the BET Family Bromodomains", J Med Chem. 54(11), Jun. 9, 2011, 3827-3838.
CID16125106—"4-(4-aminophenyl)-1H-indazol-3-amine", (2007) National Center for Biotechnology Information. PubChem Compound Database; CID=16125106, https://pubchem.ncbi.nlm.nih.gov/compound/16125106.

(56) References Cited

OTHER PUBLICATIONS

CID21042819, National Center for Biotechnology Information. PubChem Compound Database; CID=21042819, https://pubchem.ncbi.nlm.nih.gov/compound/21042819 (accessed Feb. 7, 2016).
Ciechanover, A. et al., "Ubiquitin-mediated proteolysis: biological regulation via destruction", BioEssays, 22:442-451 (2000).
Clackson, T. et al. "Redesigning an FKBP-ligand interface to generate chemical dimerizers with novel specificity", Proc Natl Acad Sci USA 95, 10437-10442 (1998).
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antagonists of inhibitors of apoptosis proteins based on thiazole amide isosteres", Bioorg. Med. Chem. Lett., 20(7), 2229-2233 (2010).
Collins, MA., et al., "Kras as a key oncogene and therapeutic target in pancreatic cancer", Frontiers in Physiol. Jan. 21, 2014; 4:407.
Connor, C.E., et al., "Circumventing tamoxifen resistance in breast cancers using antiestrogens that induce unique conformational changes in the estrogen receptor", Cancer Res. 61: 2917-2922 (2001).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692.
Crews, C. M., "Targeting the undruggable proteome: the small molecules of my dreams", Chem Biol 17, 551-555, doi:S1074-5521(10)00196-1 [pii] 10.1016/j.chembiol.2010.05.011 (2010).
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Dassonville, O., et al., "EGFR targeting therapies: Monoclonal antibodies versus tyrosine kinase inhibitors", Critical Reviews in Oncology/Hematology 62, 53-61 (2007).
Dawson, et al., "Inhibition of BET recruitment to chromatin as an effective treatment for MLL-fusion leukemia", Nature 478, Oct 2, 2011, 529-533.
Dejarnette, J. B. et al., "Specific requirement for CD3epsilon in T cell development", Proc Natl Acad Sci USA 95, 14909-14914 (1998).
Delmore, J.E. et al., "BET Bromodomain inhibition as a therapeutic strategy to target c-Myc", Cell, 146 (2011) 904-917.
Deroo, B.J., et al., "Estrogen receptors and human disease", Journal of Clinical Investigation, (2006), vol. 116(3), pp. 561-570.
Deshaies, R.J., "SCF and Cullin/RING H2-based ubiquitin ligases", Annu. Rev. Cell Dev. Biol., 15:435-467 (1999).
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. Curr Opin Chem Biol 13, 549-555, doi:S1367-5931(09)00107-0 [pii] 10.1016/j.cbpa.2009.08.003 (2009).
Douglass, E.F., et al., "A Comprehensive Mathematical Model for Three-Body Binding Equilibria", J Am Chem Soc 135, 6092-6099 (2013).
Drilon, A., "MET Exon 14 Alterations in Lung Cancer: Exon Skipping Extends Half-Life", Clinical Cancer Research 22, 2832-2834 (2016).
Dvorin, J.D., et al. "A Plant-Like Kinase in Plasmodium falciparum Regulates Parasite Egress from Erythrocytes", Science. vol. 328, May 14, 2010 910-912.
Elofsson, et al., "Towards subunit-specific proteasome inhibitors: synthesis and evaluation of peptide alpha',beta'-epoxyketones", Chem Biol 6, 811-822, doi:S1074-5521(99)80128-8 [pii] (1999).
El-Shami, et al., "FLT3 inhibitors in acute myeloid leukemia", Expert Rev. Hemalol. 1(2) 153-160 (2008).
Engleman, J.A., et al., <em>MET</em> "Amplification Leads to Gefitinib Resistance in Lung Cancer by Activating ERBB3 Signaling", Science 316, 1039-1043 (2007).
Felici, et al., "Beta-Cyclodextrin-Appended giant amphiphile: aggregation to vesicle polymersomes and immobilizations of enzymes", Chemistry 14(32), 2008 9914-9920 (CAPLUS record).
Field, S.D., et al., "Selective Downregulation of JAK2 and JAK3 by an ATP-Competitive pan-JAK Inhibitor", ACS Chem Biol 12, 1183-1187 (2017).
Filippakopoulos, et al., "Selective inhibition of BET bromodomains", Nature 468, Dec. 23, 2010, 1067-1073.
Finlay, M. et al., "Discovery of a potent and selective EGFR inhibitor (AZD9291) of both sensitizing and T790M resistance mutations that spares the wild type form of the receptor", Journal of Medicinal Chemistry 2014, 57 (20), 8249-8267.
Finnin, et al., "Structures of a histone deacetylase homologue bound to the TSA and SAHA inhibitors", Nature 401, Sep. 9, 1999, 188-193.
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 (2010).
Forastiere, et. al., "Use of Paclitaxel (TAXOL) in squamous cell carcinoma of the head and neck", Sem. Oncol., 20:56-60, 1993.
French, C.A. et al., "BRD-NUT oncoproteins: a family of closely related nuclear proteins that block epithelial differentiation and maintain the growth of carcinoma cells", Oncogene, 27 (2008) 2237-2242.
Fruchtel, et al., "Organic Chemistry on Solid Supports", Agnew. Chem. Int. Ed. Engl. 35, 17-42.
Fung, "Structure Guided Discovery of Inhibitors of Indoleamine 2,3-dioxygenase (IDOL)", University of Auckland 1-244 (2015).
Gabay, M. et al., "MYC Activation is a hallmark of cancer initiation and maintenance", Cold Spring Harbor Laboratory Press, Perspect Med. 4:a014241 1-14 (2014).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
GenBank: AAV70825.1, "HT2 [Expression vector pHT2]". Dec. 1, 2004 http://www.ncbi.nlm.nih.gov/protein/AAV70825.1—1 page.
GenBank: ADN27525.1, "HaloTag protein [HaloTag control vector]". Sep. 21, 2010 http://www.ncbi.nlm.nih.qov/protein/ADN27525.1—1 page.
Gething, M. J. "Role and regulation of the ER chaperone BiP", Semin Cell Dev Biol 10, 465-472, doi:S1084-9521(99)90318-X [pii] 10.1006/scdb.1999.0318 (1999).
Gheradi, E., et al., "Targeting MET in cancer: rationale and progress", Nat Rev Cancer 12, 89-103 (2012).
Gies, E. et al., "Niclosamide prevents the formation of large ubiquitin-containing aggregates caused by proteasome inhibition", PLoS One 5, e14410, doi:10.1371/journal.pone.0014410 1-11 (2010).
Goldstein, et al. "Biological Efficacy of a Chimeric Antibody to the Epidermal Growth Factor Receptor in a Human Tumor", (1995), Clin Cancer Res. vol. 1, Nov. 1995, 1311-1318.

(56) References Cited

OTHER PUBLICATIONS

Goode, et al., "Identification of Promiscuous Small Molecule Activators in High-Throughput Enzyme Activation Screens", J. Med. Chem. 2008, 51, 2346-2349.
Gosink, M et al., "Redirecting the specificity of ubiquitination by modifying ubiquitin-conjugating enzymes", Pro. Natl. Acad Sci, vol. 92, pp. 9117-9121, 1995.
Graves, Lee M., et al, "The dynamic nature of the kinome", Biochemical Journal, Feb. 15; 450(1), 1-8 (2013).
Green, M.C. et al, "Monoclonal Antibody Therapy for Solid Tumors", Cancer Treat. Rev., (2000), 26(4), 269-286.
Griffith, E., et al., "Methionine aminopeptidase (type 2) is the common target for angiogenesis inhibitors AGM-1470 and ovalicin", Chem. Biol., 4:461-471 (1997).
Gschwind, A., et al., "The discovery of receptor tyrosine kinases: targets for cancer therapy", Nat Rev Cancer 4, 361-370 (2004).
Guo C., et. al, "Design of oxobenzimidazoles and oxindoles as novel androgen receptor antagonists", Bioorganic & Medicinal Chemistry Letters, 2012, 22:2572-2578.
Guo, C. et al "Discovery of Aryloxy Tetramethylcyclobutanes as Novel Androgen Receptor Antagonists", J. Med. Chem. 2011, 54, 7693-7704.
Gustafson, et al., "Small-Molecule-Mediated Degradation of the Androgen Receptor through Hydrophobic Tagging", Agnew Chem Int Ed., 54: 9659-9662.
Hanan, et al, "Discovery of selective and noncovalent diaminopyrimidine-based inhibitors of epidermal growth factor receptor containing the T790M resistance mutation", J. Med Chem. 57(23), 2014, 10176-10191.
Hanisak, et al., "Efforts toward the optimization of a bi-aryl class of potent IRAK4 inhibitors", Bioorg Med Chem Lett 1;26(17) 4250-4255 (2016).
Hatakeyama, et al., "Ubiquitin-dependent degradation of IkBa is mediated by a ubiquitin ligase Skpl/Cul 1/f-box protein FWD1", PNAS USA (1999) 96: 3859-3863.
Haupt, Y. et al., "Mdm2 promotes the rapid degradation of p53", Nature 387, 296-299 (1997).
Heinlein, Chang C. "Androgen receptor in prostate cancer", Endocr Rev. Apr. 2004;25(2):276-308. Review. PubMed PMID: 15082523.
Heinlein, Chang C., "The roles of androgen receptors and androgen-binding proteins in nongenomic androgen actions", Mol Endocrinol. Oct. 2002; 16(10):2181-2187. Review. PubMed PMID: 12351684.
Heldring, et al., "Estrogen Receptors: How Do They Signal and What are Their Targets", Physiological Reviews (2007), vol. 87, pp. 905-931.
Hennessy, EJ, et al., "Discovery of aminopiperidine-based Smac mimetics as IAP antagonists", Bioorg. Med. Chem. Lett., 22(4), 1690-1694 (2012).
Herm-Gotz, A. et al., "Rapid control of protein level in the apicomplexan Toxoplasma gondii", Nat Methods 4, 1003-1005, doi:nmeth1134 [pii] 10.1038/nmeth1134 (2007).
Hewings, et al., "3,5-Dimethylisoxazoles Act As Acetyllysine-mimetic Bromodomain", J Med Chem. 54(19), Oct. 13, 2011, 6761-6770.
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hjerpe, R., et al., "Efficient protection and isolation of ubiquitylated proteins using tandem ubiquitin-binding entities", EMBO reports 10, 1250-1258 (2009).
Ho, K. et al., "Discovery of 4-phenyl-2-phenylaminopyridine based TNIK inhibitors", Bioorganic and Medicinal Chemistry Letters 2013, 23, 569-573.
Holford, et al., "Understanding the Dos-Effect Relationship: Clinical Application of Pharmacokinetic-Pharmacodynamic Models", Clinical Pharmacokinetics, 6:429-453 (1981).

Hollstein, et al., "p53 mutations in human cancers", Science, 253, 49-53 (1991).
Holmes, et al., "Phase II trial of taxol, an active drug in the treatment of metastatic breast cancer", J. Nat. Cancer Inst., 83:1797,(1991).
Hon, et al., "Structural basis for the recognition of hydroxyproline in Hlf-1 alpha by pVHL", Nature 417, Jun. 27, 2002, 975-978.
Iqbal, N., "Human Epidermal Growth Factor Receptor 2 (HER2) in Cancers: Overexpression and Therapeutic Implications", Molecular Biology International 2014 Article ID 852748 (2014).
Irak-1-4 Inhibitor I, PubChem (2007); National Center for Biotechnology Information. PubChem Compound Database; CID-11983295, https://pubchem.ncbi.nlm.nih.gov/compound/11983295.
Ishikawa, T. et al., "Design and synthesis of novel human epidermal growth factor receptor 2 (HER2)/epidermal growth factor receptor (EGFR) dual inhibitors bearing a pyrrolo[3,2-d]pyrimidine scaffold", Journal of Medicinal Chemistry 2011, 54 (23), 8030-8050.
Ivan, M., et al., "HIFa Targeted for VHL-Mediated Destruction by Proline Hydroxylation: Implications for O2 Sensing", Science, vol. 292, No. 5516, pp. 464-468, 2001.
Iwamoto, M., et al., "A general chemical method to regulate protein stability in the mammalian central nervous system", Chem Biol 17, 981-988, doi:S1074-5521(10)00305-4 [pii] 10.1016/j.chembiol.2010.07.009 (2010).
Jackson, S.P., "DNA-dependent protein kinase", International Journal of Biochemistry and Cell Biology. 29 (7):935-8 (1997).
Jang, E.R. et al., "Targeted Degradation of Proteins by PROTACs," Curr. Protoc. Chem. Biol., 2010, vol. 2, No. 2, pp. 71-87.
Janssens, S., et al. "Functional Diversity and Regulation of Different Interleukin-1 Receptor-Associated Kinase (IRAK) Family Members", Mol. Cell. 11(2), 2003, 293-302.
Jiang, et al., "Synthesis of 7alpha-substituted derivatives of 17beta-estradiol", Steroids 71(5), May 2006, 334-342 (Abstract).
Jo, M., et al., "Cross-talk between Epidermal Growth Factor Receptor and c-Met Signal Pathways in Transformed Cells", J Biol Chem 275, 8806-8811 (2000).
Joffre, C., et al., "A direct role for Met endocytosis in tumorigenesis", Nat Cell Biol 13, 827-837 (2011).
Jordan, V.C. et al., "A monohydroxylated metabolite of tamoxifen with potent antioestrogenic activity", Endocrinol 75: 305-316 (1977).
Jortzik, et al., "Benzo[b]quinolizinium Derivatives Have a Strong Antimalarial Activity and Inhibit Indoleamine Dioxgenase" Antimicrobial Agents and Chemotherapy, 60:1 115-125 (2016).
Jung, M. E. et al "Structure-Activity Relationship for Thioydantoin Androgen Receptor Antagonists for Castration-Resistant Prostate Cancer (CRPC)", J. Med. Chem. 2010, 53, 2779-2796.
Kanakaraj, et al, "Interleukin (IL)-1 Receptor-associated Kinase (IRAK) Requirement for Optimal Induction of Multiple IL-1 Signaling Pathways and IL-6 Production", J. Exp. Med. 187(12), 1998, 2073-2079.
Kanakaraj, et al. "Defective Interleukin (IL)-18-mediated Natural Killer and T Helper Cell Type 1 Responses in IL-1 Receptor-associated Kinase (IRAK)-deficient Mice", J. Exp. Med. 189(7), 1999, 1129-1138.
Karin, M., et al., "Phosphorylation meets ubiquitination: the control of NF-kB Activity", Annu. Rev. Immunol., 18:621-663 (2000).
Karlas, a. et al. "Genome-wide RNAi screen identifies human host factors crucial for influenza virus replication", Nature 463, 818-822, doi:nature08760 [pii] 10.1038/nature08760 (2010).
Kawagoe, T, et al. "Essential role of IRAK-4 protein and its kinase activity in Toll-like receptor-mediated immune responses but not in TCR signaling", J. Exp. Med. 204(5): 2007, 1013-1024.
Kearns, C.M. et. al., "Paclitaxel pharmacokinetics and pharmacodynamics", Seminars in Oncology, vol. 22, No. 3, Suppl 6, 1995, 16-23.
Kermorgant, S., et al., "Protein Kinase C Controls Microtubule-based Traffic but Not Proteasomal Degradation of c-Met", J Biol Chem 278, 28921-28929 (2003).
Kim, et al., "Heat shock protein as molecular targets for breast cancer therapeutics", J. Breast Cancer. 14(3), Sep. 2011, 167-174.
Kim, K.S., "Discovery of tetrahydroisoquinoline-based bivalent heterodimeric IAP antagonists", Bioorg. Med. Chem. Lett. 24(21), 5022-5029 (2014).

(56) References Cited

OTHER PUBLICATIONS

Kim, Kyung Bo, et al., "Development and characterization of proteasome inhibitors", Methods Enzymol 399, 585-609 (2005).
Kim, T W, et al., "A critical role for IRAK4 kinase activity in Toll-like receptor-mediated innate immunity", J. Exp. Med 204(5), 2007, 1025-1036.
Kirikoshi, H. et al. "Molecular cloning and characterization of human Frizzled-4 on chromosome 11q14-q21", Biochem Biophys Res Commun 264, 955-961, doi:10.1006/bbrc.1999.1612 50006-291X(99)91612-1 [pii] (1999).
Kiyoi, "FLT3 inhibitors; recent advances and problems for clinical application", Nagoya J Med, Sci. 77. 7-17 (2015).
Klapproth, K. et al., "Advances in the understanding of MYC-induced lymphomagenesis", British journal of hematology, 149 (2010) 484-497.
Knickelbein, K., et al., Mutant KRAS as a critical determinant of the therapeutic response of colorectal cancer, Genes Dis. Mar. 2015; 2(1):4-12.
Knott, Edward (1955). "Compounds containing sulphur chromophores. Part I. The action of bases on heterocyclic sulphide quarternary salts", Journal of the Chemical Society (resumed). 10.1039/jr9550000916. 949-954) (USPTO summary attached).
Koch, P. et al., "Inhibitors of c-Jun N-Terminal kinases: an update", in Journal of Medicinal Chemistry 2015, 58, 72-95.
Koga, F., et al., "Low Dose Geldanamycin Inhibits Hepatocyte Growth Factor- and Hypoxia-Stimulated Invasion of Cancer Cells", Cell Cycle 6, 1393-1402 (2007).
Koh, E. Y. et al., "Novel retroviral vectors to facilitate expression screens in mammalian cells", Nucleic Acids Res 30, e142 (2002) 1-7.
Kohl, et al., "Inhibition of farnesyltransferase induces regression of mammary and salivary carcinomas in ras transgenic mice", Nat Med. 1(8):792-797 (1995).
Konecny, G.E., et al., "Activity of the Dual Kinase Inhibitor Lapatinib (GW572016) against HER-2-Overexpressing and Trastuzumab-Treated Breast Cancer Cells", Cancer Research 66, 1630-1639 (2006).
Kong-Beltran, M., et al., "Somatic Mutations Lead to an Oncogenic Deletion of Met in Lung Cancer", Cancer Research 66, 283-289 (2006).
Koziczak-Holbrom, et al., "IRAK-4 Kinase Activity is Required for Interleukin-1 (IL-1) Receptor-and Toll-like Receptor 7-mediated Signaling and Gene Expression", J. Biol. Chem. 282(18): 2007; 13552-13560.
Krishnan, M. N. et al. "RNA interference screen for human genes associated with West Nile virus infection", Nature 455, 242-245, doi:nature07207 [pii] 10.1038/nature07207 (2008).
Kronke, et al, "Lenalidomide Causes Selective Degradation of IKZF1 and IKZF3 in Multiple Myeloma Cells", Science 343, 301-305 (2014).
Kubota, H. "Quality control against misfolded proteins in the cytosol: a network for cell survival", J Biochem 146, 609-616, doi:mvp139 [pii] 10.1093/jb/mvp139 (2009).
Kuntz, K.W. et al., "The importance of being me: magic methyls, methyltransferase inhibitors, and the discovery of tazemetostat", in the Journal of Medicinal Chemistry 2016, 59, 1556-1564.
Kurimchak, A. M. et al.,"Resistance to Bet Bromodomain Inhibitors is Mediated by Kinome Reprogramming in Ovarian Cancer", Cell Reports 16, 1273-1286 (2016).
Kwon, YT., et al., "Bivalent inhibitor of the N-end Rule Pathway", J. Biol. Chem., vol., 274, No. 25, pp. 18135-18139, 1999.
Lackey, K. et al., "The discovery of potent cRaf1 kinase inhibitors", Bioorganic and Medicinal Chemistry Letters, 10 (2000), 223-226.
Lai, A.C., et al., "Modular PROTAC Design for the Degradation of Oncogenic BCR-ABL", Angew Chem Int Ed Engl 55, 807-810 (2016).
Lebraud, H., et al., "Protein Degradation by In-Cell Self-Assembly of Proteolysis Targeting Chimeras", ACS Central Science, 2, 927-934 (2016).

Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Lelais, G. et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a novel, potent, and WT sparing covalent inhibitor of oncogenic (L858R, ex19del) and resistant (T790M) EGFR mutants for the treatment of EGFR mutant non-small-cell lung cancers", Journal of Medicinal Chemistry 2016, 59(14), 6671-6689.
Lemmon, M.A., et al., "Cell Signaling by Receptor Tyrosine Kinases", Cell 141, 1117-1134 (2010).
Leu, et al., "HSP70 inhibition by the small-molecule 2-phenylethynesulfonaminde impairs protein clearance pathways in tumor cells", Mol. Cancer Res. 9(7), Jul. 2011, 936-947.
Li, et al. "Mutant Cells That do not respond to Interleukin-1 (IL-1) Reveal a Novel Role for IL-1 Receptor-Associated Kinase", Mol. Cell. Biol. 19(7), 1999, 4643-4652.
Li, S., et al. "IRAK-4: A novel member of the IRAK family with the properties of an IRAK-kinase", Proc. Natl. Acad. Sci. USA 99(8), 2002, 5567-5572.
Li, X. et al., "Amino-terminal protein processing in *Saccharomyces cerevisiae* is an essential function that requires two distinct methionine aminopeptidases", Proc. Natl. Acad. Sci. USA, 92:12357-12361 (1995).
Li, Yan, et al., "Single polymer-drug conjugate carrying two drugs for fixed-dose co-delivery", Medicinal Chemistry, 2014, vol. 4(10): 676-683.
Lim, et al "Discovery of 5-Amino-N-(1H-pyrazol-4-yl)pyrazolo[1,5-a]pyrimidine-3-carboxamide inhibitors of IRAK4", ACS Med Chem Lett 6: 683-688 (2015).
Link, V. et al., "Proteomics of early zebrafish embryos", BMC Dev Biol 6, 1, doi:1471-213X-6-1 [pii] 10.1186/1471-213X-6-1 (2006).
Lins, L. et al., "The hydrophobic effect in protein folding", FASEB J9, 535-540 (1995).
Littlejohn, Tamantha Kim, "Studies on human indoleamie 2,3-dioxygenase (IDO)", Doctor of Philosophy Thesis, Faculty of Sciences, University of Wollongong, 2001.
Liu, et al., "Discovery of a 2,4-diamino-7-aminoalkoxyquinazoline as a potent and selective inhibitor of histone lysine methyltransferase G9a", J Med Chem. 52(24), Dec. 24, 2009, 7950-7953.
Liu, Hong, et al., "Bioactivation of the selective estrogen receptor modulator desmethylated arzoxifene to quinoids: 4'-fluoro substitution prevents quinoid formation", Chem. Res. Toxicol. 2005, 18, 162-173.
Liu, K., et al., "Design and biological characterization of hybrid compounds of curcumin and thalidomide for multiple myeloma", Org. Biomol. Chem. 2013, 11, 4757-4763.
Liu, S., et al., "Structure of human methionine aminopeptidase-2 complexed with fumagillin", Science, 282: 1324-1327 (1998).
Llinas-Brunet, et al., "Discovery of a potent and selective noncovalent linear inhibitor of the hepatitis C virus NS3 protease (BI 201335)", J Med Chem. 53(17), Sep. 9, 2010, 6466-6476.
Loewe & Muischnek, 1926, arch. Exp. Pathol Pharmaol 114:313-326 (not in English).
Lopez-Girona, A. et al., Cereblon is a direct protein target for immunomodulatory and antiproliferative activities of lenalidomide and pomalidomide, Leukemia 26: 2326-2335, 2012).
Los, G. V. et al., "HaloTag: A novel protein labeling technology for cell imaging and protein analysis", ACS Chemical Biology, vol. 3(6): 373-382, Jun. 6, 2008.
Lountos, et al., "Structural Characterization of Inhibitor Complexes with Checkpoint Kinase 2 (Chk2), a Drug Target for Cancer Therapy", J Struct Biol.176(3), Dec. 2011, 292-301.
Loven, J. et al., "Selective Inhibition of Tumor Oncogenes by Disruption of Super Enhancers", Cell, 153 (2013) 320-334.
Lu, et al., "Hijacking the E3 ubiquitin ligase cereblon to efficiently targe BRD4", Chem Biol 22(6), 2015, 755-763.
Lu, et al., "The myeloma drug lenalidomide promotes the cereblon-dependent destruction of ikaros proteins", Science 343, 305-309 (2014).

(56) References Cited

OTHER PUBLICATIONS

Lu, NZ, et al., "International Union of Pharmacology. LXV. The pharmacology and classification of the nuclear receptor superfamily: glucocorticoid, mineralocorticoid, progesterone, and androgen receptors", Pharmacol Rev. Dec. 2006;58(4):782-797. Review. PubMed PMID: 17132855.

Luo, J. et al. "A genome-wide RNAi screen identifies multiple synthetic lethal interactions with the Ras oncogene", Cell 137, 835-848, doi:S0092-8674(09)00529-7 [pii] 10.1016/j.cell.2009. 05.006 (2009).

Lyapina, S.A., et al., "Human CUL1 forms an evolutionarily conserved ubiquitin ligase complex (SCF) with SKP1 and an F-box protein", Proc. Natl. Acad. Sci. USA, 95:7451-7456 (1998).

Lye, E. et al, "The role of interleukin 1 receptor-associated Kinase-4 (IRAK-4) kinase activity in IRAK-4-mediated signaling", J. Biol. Chem. 279(39); 2004, 40653-40658.

Ma, Y., et al., "Targeted degradation of KRAS by an engineered ubiquitin ligase suppresses pancreatic cancer cell growth in vitro and in vivo", Mol Cancer Ther. Mar. 2013;12(3):286-94.

Macbeath, G., et al., "Printing small molecules as microarrays and detecting protein-ligand interactions en masse", J. Am. Chem. Soc., 121:7967-7968 (1999).

Mahalingam, D., et al., "Targeting HSP90 for cancer therapy", Br J Cancer 100, 1523-1529 (2009).

Maniatis, T. "A ubiquitin ligase complex essential for the Nf-Kb, Wnt/Wingless and Hedgehog signaling pathways", Genes & Development, vol. 13, pp. 505-510, 1999.

Mannhold, R., et al., "IAP antagonists: promising candidates for cancer therapy", Drug Discov. Today, 15 (5-6), 210-219 (2010).

Margottin, F., et al., "A novel human Wd protein, h-βTrCP, that interacts with HIV-1 Vpu connects CD4 to the ER degradation pathway through an F-Box motif", Mol Cell., 1:565-574 (1998).

Markman, et al., "Taxol: an important new drug in the management of epithelial ovarian cancer", Yale Journal of Biology and Medicine, 64:583-590, 1991.

Martinez-Iacaci, L., et al, "RAS transformation causes sustained activation of epidermal growth factor receptor and elevation of mitogen-activated protein kinase in human mammary epithelial cells", Int. J. Cancer (2000), 88(1), 44-52.

Masellis-Smith, a. et al., "CD9-regulated adhesion. Anti-CD9 monoclonal antibody induce pre-B cell adhesion to bone marrow fibroblasts through de novo recognition of fibronectin", J. Immunol 152, 2768-2777 (1994).

Massague, J. et al., "Serine/threonine kinase receptors: mediators of transforming growth factor beta family signals", (1996) Cancer Surveys. 27:41-64.

Mathias, L. J., et al., "Adamantane-containing polymers", Acs Sym Ser 624, 197-207 (1996).

McElroy, et al., "Discovery and hit-to-lead optimization of 2,6-diaminopyrimidine inhibitors of interleukin-1 receptor-associated kinase 4", Bioorg Med Chem Lett 25(9) 1836-1841 (2015).

McElroy, et al., "Potent and Selective Amidopyrazole Inhibitors of IRAK4 that are Efficacious in a Rodent Model of Inflammation", ACS Med Chem Lett 6: 677-682 (2015).

McGuire, et al., "Taxol: a unique antineoplastic agent with significant activity in advanced ovarian epithelial neoplasms", Ann. Intern, Med., 111:273, 1989.

Medvedev, et al. "Distinct Mutations in IRAK-4 confer hyporesponsiveness to lipopolysaccharide and interleukin-1 in a patient with recurrent bacterial infections", J. Exp. Med., 198(4), 2003, 521-531.

Mehellou Y, De Clercq E., "Twenty-six years of anti-HIV drug discovery: where do we stand and where do we go?", J Med Chem. Jan. 28, 2010;53(2):521-538. doi: 10.1021/jm900492g. Review. PubMed PMID: 19785437.

Meng, L., et al., "Epoxomicin, a ptotent and selective proteasome inhibitor, exhibits in vivo anti-inflammatory activity", Proc. Natl. Acad. Sci. USA, 96:10403-10408 (1999).

Menger, et al, "Self-adhesion among phospholipid vesicles", 2006, J. Am. Chem. Soc. 128:1414-1415.

Mercurio, et al., "IKK-1 and IKK-2: cytokine-activated IκB kinases essential for NF-κB activation", Science, 278: 860-866 (1997).

Mertz, J.A. et al., "Targeting MYC dependence in cancer by inhibiting BET bromodomains", PNAS, 108 (2011) 16669-16674.

Millan, — et al "Design and Synthesis of Inhaled p38 Inhibitors for the Treatment of Chronic Obstructive Pulmonary Disease", J Med Chem.54(22), Nov. 24, 2011, 7797-7814.

Min, Jung-hyun, et al., "Structure of an HIV-1-alpha—pVHL complex: hydroxyproline recognition in signaling", Jun. 7, 2002, 296: 1886-1889.

Miyajima, N., et al., "The HSP90 Inhibitor Ganetespib Synergizes with the MET Kinase Inhibitor Crizotinib in both Crizotinib-Sensitive and -Resistant MET-Driven Tumor Models", Cancer Research 73, 7022-7033 (2013).

Miyazaki, M et al., "Discovery of DS-5272 as a promising candidate: a potent and orally active p53-MDM2 interaction, inhibitor", Bioorg. Med. Chem. Lett. (2015) 23, 2360-2367.

Momand, et al., "The mdm-2 oncogene product forms a complex with the p53 protein and inhibits p53-mediated transactivation", Cell, 69, 1237-1245 (1992).

Muller, G., et al., "Amino- Substituted Thalodomide Analogs: Potent Inhibitors of TNF-α Production", Bioorganic & Medicinal Chemistry Letters 9 (1999) 1625-1630.

Murray, A.W., "Cell cycle extracts", Methods Cell Biol. 36:581-605 (1991).

Nagahara, H., et al., "Transduction of full-length TAT fusion proteins into mammalian cells: TAT-p27$^{Kip1}$ induces cell migration", Nat. Med., 4:1449-1452 (1998).

Nawaz, et al., "Proteasome-dependent degradation of the human estrogen receptor", PNAS USA, Mar. 1999, vol. 96, pp. 1858-1862.

Ndubaku, C, et al., "Antagonism of c-IAP and XIAP proteins is required for efficient induction of cell death by small-molecule IAP antagonists", ACS Chem Biol. Jul. 17, 2009;4(7):557-566.

Neklesa, T. K. et al., "Small-molecule hydrophobic tagging-induced degradation of HaloTag fusion proteins". Nat. Chem. Biol., vol. 7(8): 538-543, Aug. 2011.

Neklesa, T.K., et al., "Chemical biology: Greasy tags for protein removal", Nature 487, 308-309 (2012).

Nicodeme, et al., "Suppression of inflammation by a synthetic histone mimic", Nature 468, Dec. 23, 2010, 1119-1123.

Nikolovska-Coleska, et al., "Interaction of a cyclic, Bivalent Smac Mimetic with the X-linked inhibitor of apoptosis protein", Biochemistry, 2008, 47(37), pp. 9811-9824.

Nishimiura, K., et al. "An auxin-based degron system for the rapid depletion of proteins in nonplant cells", Nature Methods. vol. 6(12): 917-923, Dec. 2009.

Noel, J. Kay, Abstract C244: ' "Development of the BET Bromodomain inhibitor OTX015", Mol Cancer Ther 2013; 12(11 Suppl); C244 1-4.

Oishi, I. et al. "The receptor tyrosine kinase Ror2 is involved in non-canonical Wnt5a/JNK signaling pathway", Genes Cells 8, 645-654, doi:662 [pii] (2003).

Oliff, Allen, "Farnesyltransferase inhibitors: targeting the molecular basis of cancer", Biochim Biophys Acta. May 31, 1999; 1423(3):C19-30.

Oost, T.K. et al., "Discovery of potent antagonists of the antiapoptotic protein XIAP for the treatment of cancer", Journal of Medicinal Chemistry 2004, 47, 4417-4426.

Organ, S.L., et al., "An overview of the c-MET signaling pathway", Therapeutic Advances in Medical Oncology 3, S7-S19 (2011).

Ostrand-Rosenberg, S., "Animal models of tumor immunity, immunotherapy and cancer vaccines", Curr Opin Immunol 16, 143-150, doi:10.1016/j.coi.2004.01.003 S0952791504000068 [pii] (2004).

Ostrem, JM., et al., "Direct small-molecule inhibitors of KRAS: from structural insights to mechanism-based design", Nat Rev Drug Discov. Nov. 2016;15(11):771-785.

Overington, J. P., et al., "How many drug targets are there?", Nat Rev Drug Discov 5, 993-996, doi:nrd2199 [pii] 10.1038/nrd2199 (2006).

Pantoliano, et al., "High-density miniaturized thermal shift assgs as a general strategy for drug discovery", J Biomol Screen, 66:429-440 (2001).

(56) References Cited

OTHER PUBLICATIONS

Parada, L. F., et al., "Human EJ bladder carcinoma oncogene is homologue of Harvey sarcoma virus ras gene", Nature 297, 474-478 (1982).
Patch, R. J., et al., "Identification of Diaryl Ether-Based Ligands for Estrogen-Related Receptor a as Potential Antidiabetic Agents", J. Med. Chem. 2011, 54, 788-808.
Pellinen, T., et al., "Small GTPase Rab21 regulates cell adhesion and controls endosomal traffic of β1-integrins", The Journal of Cell Biology 173, 767-780 (2006).
Pepe, A. et. al., "Synthesis and structure-activity relationship studies of novel dihydropyridones as androgen receptor modulators", J. Med. Chem. 2013, 56, 8280-8297.
Perez, HL," Discovery of potent heterodimeric antagonists of inhibitor of apoptosis proteins (IAPs) with sustained antitumor activity", J. Med. Chem. 58(3), 1556-1562 (2015).
Perez-Torres, M., et al., "Epidermal Growth Factor Receptor (EGFR) Antibody Down-regulates Mutant Receptors and Inhibits Tumors Expressing EGFR Mutations", J Biol Chem 281, 40183-40192 (2006).
Peschard, P., et al., "Mutation of the c-Cbl TKB Domain Binding Site on the Met Receptor Tyrosine Kinase Converts It into a Transforming Protein", Molecular Cell 8, 995-1004 (2001).
Philip, P.A., et al., "Potential for protein kinase C inhibitors in cancer therapy", Cancer Treatment and Research 78: 3-27 (1995).
Picard, et al. "Pyogenic Bacterial Infections in Humans with IRAK-4 Deficiency", Science 299(5615), 2003, 2076-2079.
Pillay, V., et al., "The Plasticity of Oncogene Addiction: Implications for Targeted Therapies Directed to Receptor Tyrosine Kinases[1,2]", Neoplasia 11, 448-458 (2009).
Porteus, M., "Design and testing of zinc finger nucleases for use in mammalian cells", Methods Mol Biol 435, 47-61, doi:10.1007/978-1-59745-232-8_4 (2008).
Poutiainen, PK, et. al., "Design, synthesis, and biological evaluation of nonsteroidal cycloalkane[d]isoxazole-containing androgen receptor modulators", J. Med. Chem. 55, 6316-6327 (2012).
Powis, G., and Kozikowski A., "New Molecular Targets for Cancer Chemotherapy", ed., Paul Workman and David Kerr, CRC press 1994, London 81-95 (1994).
Prakash, et al., "Stereoselective Nucleophilic Trifluoromethylation of N-(tert-Butylsulfinyl)imines by Using Trimethyl (trifluoromethyl)silane", Angew Chem Int Ed Engl. 40(3), Feb. 2, 2001, 589-590 (Abstract).
Pratz, K.W., et al., "A pharmacodynamic study of the FLT3 inhibitor KW-2449 yields insight into the basis for clinical response", Blood 113, 3938-3946 (2009).
Prior, IA., et al., "A comprehensive survey of Ras mutations in cancer", Cancer Res. May 15, 2012; 72(10):2457-67.
Pruett-Miller, S. M., et al. "Attenuation of Zinc Finger Nuclease Toxicity by Small-Molecule Regulation of Protein Levels", PLoS Genetics. vol. 5(2): e1000376, Feb. 2009.
Puissant, A. et al., "Targeting MYCN in neuroblastoma by BET bromodomain inhibition", Cancer discovery, 3 (2013) 308-323.
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Qin, Zhihui, et al., "Benzothiophene selective estrogen receptor modulators with modulated oxidative activity and receptor affinity", J. Med Chem 2007, 50, 2682-2692.
Rago, C.et al., "Genetic knockouts and knockins in human somatic cells", Nat Protoc 2, 2734-2746, doi:nprot.2007.408 [pii] 10.1038/nprot.2007.408 (2007).
Raina, K., et al., "PROTAC-induced BET protein degradation as a therapy for castration-resistant prostate cancer", Proc Natl Acad Sci USA 113, 7124-7129 (2016).
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157. (J. Med. Chem. (2014) 57, 10499-10511 Rew, et al.).
Robinson, M. S., et al. "Rapid Inactivation of Proteins by Rapamycin-Induced Rerouting to Mitochondria", Developmental Cell. vol. 18: 324-331, Feb. 16, 2010.
Rodriguez-Gonzalez, et al., "Targeting steroid hormone receptors for ubiquitination and degradation in breast and prostate cancer", Oncogene. 27(57), Dec. 4, 2008, 7201-7211.
Rosania et al., "Targeting hyperproliferative disorders with cyclin dependent kinase inhibitors", Exp. Opin. Ther. Patents (2000) 10(2):215-230.
Ross, SJ., et al., "Targeting KRAS-dependent tumors with AZD4785, a high-affinity therapeutic antisense oligonucleotide inhibitor of KRAS", Sci Transl Med. Jun. 14, 2017;9(394).
Roth, J. et al., "Nucleo-cytoplasmic shuttling of the hdm2 oncoprotein regulates the levels of the p53 protein via a pathway used by the human immunodeficiency virus rev protein", EMBO J. (1998), 17, 554-564.
Rotili, D., et al., "Photoactivable peptides for identifying enzyme-substrate and protein-protein interactions", Chem Commun (Carob) 47(5), Feb. 2011, 1488-1490.
Roy, et al., "Regulation of androgen action", Vitam Horm. 1999;55:309-52. Review. PubMed PMID: 9949684.
Ruchelman, A., et al., "Isosteric analogs of lenalidominde and pomalidomide: Synthesis and biological activity", Bioorganic & Medicinal Chemistry Letters 23 (2013) 360-365.
Rusch, M., et al., "Identification of Acyl Protein Thioesterases 1 and 2 as the Cellular Targets of the Ras-Signaling Modulators Palmostatin B amd M", Angew. Chem. Int. Ed., 50: 9838-9842. doi:10.1002/anie.201102967 (Angew. Chem. Int. Ed. 2011, 50, 9838-9842) (2011).
Russ, A. P. et al., "The druggable genome: an update", Drug Discov Today 10, 1607-1610, doi:S1359-6446(05)03666-4 [pii] 10.1016/S1359-6446(05)03666-4 (2005).
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1 -Cullin-F box complex for ubiquitination and degradation", Proc Natl Acad Sci U S A.98(15), Jul. 17, 2001, 8554-8559.
Sargent, et al., "Synthesis of the cyclophane tetramethoxyturriane: a derivative of the phenolic cyclophanes of Grevillea striata R. Br.", J. Chem. Soc., Perkin Trans. 1, 1990, 129-132 (Abstract).
Sausville, E.A., "Cyclin-dependent kinase modulators studied at the NCI: pre-clinical and clinical studies", Cum Med. Chem. Anti-Canc Agents 3:47-56 (2003).
Scagliotti, G., et al., "Phase III Multinational, Randomized, Double-Blind, Placebo-Controlled Study of Tivantinib (ARQ 197) Plus Erlotinib Versus Erlotinib Alone in Previously Treated Patients With Locally Advanced or Metastatic Nonsquamous Non—Small-Cell Lung Cancer", Journal of Clinical Oncology 33, 2667-2674 (2015).
Scharovsky, et al., "Inhibition of ras oncogene: a novel approach to antineoplastic therapy", (2000), Journal of Biomedical Science. 7(4) 292-298.
Schenkel, et al., "Discovery of Potent and Highly Selective Thienopyridine Janus Kinase 2 Inhibitors", J Med Chem.54(24), Dec. 22, 2011, 8440-8450.
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Schrader, E. K., et al. "Making It Easier to Regulate Protein Stability", Chemistry & Biology. vol. 17: 917-918, Sep. 24, 2010.
Schubert, U., et al., "CD4 glycoprotein degradation induced by human immunodeficiency virus type 1 Vpu protein requires the function of proteasomes and the ubliquitin-conjugating pathway", J. Virol., 72:2280-2288 (1998).

(56) References Cited

OTHER PUBLICATIONS

Seganish, "Inhibitors of interleukin-1 receptor-associated kinase 4 (IRAK4): a patent review (2012-2015)", Expert Opin Ther Pat 26:8, 917-932 (2016).
Seganish, et al., "Discovery and Structure Enabled Synthesis of 2,6-Diaminopyrimidin-4-one IRAK4 Inhibitors", ACS Med Chem Lett (6) 942-947 (2015).
Sekulić, et al. "A direct linkage between the phosphoinositide 3-Kinase-AKTA signaling pathway and the mammalian target Of rapamycin in mitogen-stimulated and transformed cells", (2000) Cancer Res. 60:3504-3513.
Sequist, L.V., et al., "Randomized Phase II Study of Erlotinib Plus Tivantinib Versus Erlotinib Plus Placebo in Previously Treated Non—Small-Cell Lung Cancer", Journal of Clinical Oncology 29, 3307-3315 (2011).
Shi, J. et al., "The mechanisms behind the therapeutic activity of BET bromodomain inhabitation", Molecular cell, 54 (2014) 728-736.
Shih, C. et al., "Isolation of a transforming sequence from a human bladder carcinoma cell line", Cell 29, 161-169, doi:0092-8674(82)90100-3 [pii] (1982).
Shimamura, et al. "Efficacy of BET bromodomain inhabitation in kras-mutant non-small cell lung cancer", Clinical Cancer Research 19(22), pp. 6183-6192 (2013) DOI:10.1158/1078-0432.CCR-12-3904.
Sin, N., et al., "The anti-angiogenic agent fumagillin covalently binds and inhibits the methionine aminopeptidase, MetAP-2", Proc Natl. Acad. Sci. USA, 94:6099-6103(1997).
Sinha, S. and Corey, S.J., "Implications for Src kinases in hematopoiesis: signal transduction therapeutics", Journal of Hematotherapy and Stem Cell Research 8 (5): 465-480 (1999).
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Smithgall, T.E., "SH2 and SH3 domains: potential targets for anti-cancer drug design", Journal of Pharmacological and Toxicological Methods. 34(3) 125-132 (1995).
So, MK. et al., "HaloTag Protein-mediated Specific Labeling of Living Cells with Quantum Dots", Biochemical and Biophysical Research Communications, 2008, vol. 374, No. 3, pp. 419-423.
Solca, F., et al., "Target Binding Properties and Cellular Activity of Afatinib (BIBW 2992), an Irreversible ErbB Family Blocker", J Pharmacol Exp Ther 343, 342-350 (2012).
Soucy, T.A., et al., "An inhibitor of NEDD8-activating enzyme as a new approach to treat cancer", Nature 458, 732-736 (2009).
Sow, et al., "Synthesis of RGD amphiphilic cyclic peptide as fibrinogen or fibronectin antagonist", Letters in Peptitde Science, 4(4/5/6) 1997, 455-461 (CAPLUS record).
Staschke et al. "IRAK4 kinase activity is required for Th17 differentiation and TH17-mediated disease", The Journal of Immunology, 183(1), 2009, 568-577.
Stern, David, "Tyrosine Kinase Signalling in Breast cancer ErbB Family Receptor Tyrosine Kinases", Breast cancer Res., 2000, 2(3), 176-183.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Stuhlmiller, Timothy J., et al., "Inhibition of Lapatinib-Induced Kinome Reprogramming in ERBB2-Positive Breast Cancer by Targeting BET Family Bromodomains", Cell Reports 11, 390-404 (2015).
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Suzuki et al. "Severe impairment of interleukin-1 and toll-like receptor signaling in mice lacking IRAK-4", Nature, 416(6882), 2002, 750-756.
Tae, H.S. et al., "Identification of Hydrophobic Tags for the Degradation of Stabilized Proteins", Chembiochem, 2012, vol. 13, No. 4, pp. 538-541.
Takayama, et al., "Detection of cytochrome P450 substrates by using a small-molecule droplet array on an NADH-immobilized solid surface", Chembiochem. 12(18), Dec. 16, 2011, 2748-2752.
Takeuchi, et al., "Receptor Tyrosine Kinases and Targeted Cancer Therapeutics", Biol Pharm Bull 34, 1774-1780 (2011).
Tallarida, et al., "Testing for Synergism Over a Range of Fixed Ratio Drug Combinations: Replacing the Isobologram", Life Sciences, vol. 58, No. 2, 23-28.
Thelemann, A., Petti, F., Griffin, G., Iwata, K., Hunt, T., Settinari, T., Fenyo, D., Gibson, N., and Haley, J.D. (2005). "Phosphotyrosine Signaling Networks in Epidermal Growth Factor Receptor Overexpressing Squamous Carcinoma Cells", Molecular & Cellular Proteomics 4.4, 356-376.
Trewartha D, Carter K. "Advances in prostate cancer treatment", Nat Rev Drug Discov. Nov. (2013);12(11):823-824. doi: 10.1038/nrd4068. PubMed PMID: 24172327.
Tsao, et al., "Hepatocyte growth factor is predominantly expressed by the carcinoma cells in non—small-cell lung cancer", Human Pathology 32, 57-65 (2001).
Tsuzuki, N., et al. "Adamantine as a Brain-Directed Drug Carrier for Poorly Absorbed Drug. 2. AZT Derivatives Conjugated with the 1-damantine Moiety", Journal of Pharmaceutical Sciences. vol. 83(4): 481-484, (1994).
Tumey, et al., "Identification and optimization of indolo[2,3-c]quinolone inhibitors of IRAK4", Bioorg Med Chem Lett 24(9) 2066-2072 (2014).
Vahid, F., et al., "The role dietary of bioactive compounds on the regulation of histone acetylases and deacetylases: A review", Gene, 562, (2015), 8-15.
Vallee, et al., "Tricyclic Series of Heat Shock Protein 90 (HSP90) Inhibitors Part I: Discovery of Tricyclic Imidazo [4,5- c] Pyridines as Potent Inhibitors of the Hsp90 Molecular Chaperone", J Med Chem. 54(20), Oct. 27, 2011, 7206-7219.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Eis, et al., "2,6-Naphthyridines as potent and selective inhibitors of the novel protein kinase C isozymes", Bioorg Med Chem Lett.21(24), Dec. 15, 2011, 7367-7372.
Van Molle, et al., "Dissecting fragment-based lead discovery at the von Hippel-Lindau protein:hypoxia inducible factor 1a protein-protein interface", Chem Biol. 19(10) Oct. 26, 2012, 1300-1312.
Vassilev, et al., "In vivo activation of the p53 pathway by small-molecule antagonists of MDM2", Science 303, Feb. 6, 2004, 844-848.
Vazquez, a. et al., "The genetics of the p53 pathway, apoptosis and cancer therapy", Nat. Rev. Drug. Dis., 7, 979-982 (2008).
Vlahos, et al. "A specific inhibitor of phosphatidylinositol 3-kinase, 2-(4-morpholinyl)-8-phenyl-4H-1-benzopyran-4-one (LY294002)", J. Biol. Chem. 269:5241-5248 (1994).
Vogelstein, et al., "Surfing the p53 network", Nature, 408, 307-310 (2000).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.

(56) References Cited

OTHER PUBLICATIONS

Wang, S., et al., Cancer cells harboring MET gene amplification activate alternative signaling pathways to escape MET inhibition but remain sensitive to Hsp90 inhibitors, Cell Cycle 8, 2050-2056 (2009).
Weinmann, H., "Cancer Immunotherapy: Selected Targets and Small-Molecule Modulators", ChemMedChem (2016), 11, 450-466.
Weisberg, et al. "Discovery and characterization of novel mutant FLT3 kinase inhibitors", Mol Cancer Ther. Sep. 2010; 9(9): 2468-2477. Doi:10.1158/1535-7163.MCT-10-0232.
Weissman, A., "Regulating protein degradation by ubiquitination", Immunology Today, vol. 18, No. 4, pp. 189-198, (1997).
Whitehead, K.A., et al., "Knocking down barriers: advances in siRNA delivery", Nat Rev Drug Discov 8, 129-138, doi:nrd2742 [pii] 10.1038/nrd2742 (2009).
Wietek C., et al, "IRAK-4: a new drug target in inflammation, sepsis, and autoimmunity", Mol. Interv. 2: 2002, 212-215.
Willson, T.M. et al., "3-[4-(1,2-Diphenylbut-l-Enyl)Phenyl] Acrylic Acid: A non-steroidal estrogen with functional selectivity for bone over uterus in rats", Journal of Medicinal Chemistry, American Chemical Society, US May 25, 1994, vol. 37 No. 11, pp. 1550-1552.
Winston, J., et al., "A family of mammalian F-box proteins", Curr. Bio., 9:1180-1182 (1999).
Winter, et al., "Phthalimide Conjugation as a strategy for in vivo target protein degradation", Science, 2015 vol. 348 (6241), pp. 1376-1381 [Pub online: May 21, 2015].
Wislez, M., et al. "Mutations at the splice sites of exon 14 of MET gene: a new target for sarcomatoid carcinomas?", Annals of Translational Medicine 4(5):96 (2016).
Woo, et. al., "Taxol inhibits progression of congenital polycystic kidney disease", Nature, 750-753, 1994.
Wood, K., et al., "Prognostic and Predictive Value in KRAS in Non-Small-Cell Lung Cancer: A Review", JAMA Oncol. Jun. 1, 2016;2(6):805-12.
Wright, et al., "Structure-Activity Relationships in Purine-Based Inhibitor Binding to HSP90 Isoforms", Chem Biol. 11 (6), Jun. 2004, 775-785.
Wu, et al. "The p53-mdm-2 autoregulatory feedback loop", Genes Dev. (1993) 7, 1126-1132.
Wurz, R. et al., "Oxopyrido[2,3-d]pyrimidines as covalent L858R/T790M mutant selective epidermal growth factor receptor (EGFR) inhibitors", ACS Medicinal Chemistry Letters 2015, 6, 987-992.
Wyce, a. et al., "Inhibition of BET bromodomain proteins as a therapeutic approach in prostate cancer", Oncotarget, 4 (2013) 2419-2429.
Xie, T., et al., "Pharmacological targeting of the pseudokinase Her3", Nat Chem Biol 10, 1006-1012 (2014).
Xu, A.M., et al., "Receptor Tyrosine Kinase Coactivation Networks in Cancer", Cancer Research 70, 3857-3860 (2010).
Xu, S. et al., "Design, synthesis and biological evaluation of new molecules inhibiting epidermal growth factor receptor threonine $^{790}$ — methionine $^{790}$ mutant", Medicinal Chemistry Communications 2012, 3, 1155-1159.
Xu, T. et al., "C5-substituted pyrido[2,3-d]pyrimidin-7-ones as highly specific kinase inhibitors targeting the clinical resistance-related EGFR$^{T790M}$mutant", Medicinal Chemistry Communications 2015, 6, 1693-1697.

Yamamoto, T., et al., "Ras-Induced transformation and signaling pathway", Journal of Biochemistry 126 (5) 799-803 (1999).
Yang, et al., "Signaling events inducted by lipopolysaccharide-activated toll-like receptor 2", J. Immunol. 163(2), 1999, 639-643.
Yaron, A., et al., "Identification of the receptor component of the IkBa-ubiquitin ligase", Nature, Bol 396, No. 6711, pp. 590-594, (1998).
Yaron, A., et al., "Inhibition of NF-κB cellular function via specific targeting of the IκB-ubiquitin ligase", EMBO J., 16:64866494 (1997).
Yasuda, H., et al., "Structural, Biochemical, and Clinical Characterization of Epidermal Growth Factor Receptor (EGFR) Exon 20 Insertion Mutations in Lung Cancer", Science Translational Medicine 5, 216ra177-216ra177 (2013).
Yeh, E., et al., "Ubiquitin-like proteins: new wines in new bottles", Gene, vol. 248, No. 1-2, pp. 1-14, (2000).
Yeh, J., et al., "The antiangiogenic agent TNP-480 requires p53 and P21 $^{CIP/WAF}$for endothelial cell growth arrest", Proc. Natl. Acad. Sci. USA, 97:12782-12787 (2000).
Yewale, C., et al., "Epidermal growth factor receptor targeting in cancer: A review of trends and strategies", Biomaterials 34, 8690-8707 (2013).
You, A.J., et al., "A miniaturized arrayed assay format for detecting small molecule-protein interactions in cells", Chem. Biol., 4:969-975 (1997).
Yuan, TL., et al., "Development of siRNA payloads to target KRAS-mutant cancer", Cancer Discov. Oct. 2014;4(10):1182-1197.
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zheng, N., et al., "Structure of a c-Cbl-UbcH7 Complex: RING Domain Function in Ubiquitin-Protein Ligases", Cell, vol. 102, No. 4, pp. 533-539, (2000).
Zhong, H. et al, "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics", Cancer res, (2000) 60(6), 1541-1545.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. (DOI:10.1021/acs.jmedchem.6b01816) (2017).
Zhou, P., et al., "Harnessing the Ubiquitination Machinery to Target the Degradation of Specific Cellular Proteins", Mol. Cell, 6:751-756 (2000).
Zillhardt, M., et al., "Foretinib (GSK1363089), an Orally Available Multikinase Inhibitor of c-Met and VEGFR-2, Blocks Proliferation, Induces Anoikis, and Impairs Ovarian Cancer Metastasis", Clinical Cancer Research 17, 4042-4051 (2011).
Zuber, J. et al., "RNAi screen identifies Brd4 as a therapeutic target in acute myeloid leukemia", Nature, 478 (2011) 524-528.

* cited by examiner

COMPOUNDS

CROSS-REFERENCE TO RELATED APPLICATIONS

This application is filed pursuant to 35 USC 371 as a United States National Phase Application of International Patent Application Serial No. PCT/EP2014/063901 filed on Jul. 1, 2014, which claims priority from 1311891.4 filed on Jul. 3, 2013 in the United Kingdom.

FIELD OF THE INVENTION

The present invention relates to compounds, compositions, combinations and medicaments containing said compounds and processes for their preparation. The invention also relates to the use of said compounds, combinations, compositions and medicaments, for example as inhibitors of the activity of the estrogen receptor, for example by degrading the estrogen receptor, the treatment of diseases and conditions mediated by the estrogen receptor, in particular for the treatment of breast cancer.

BACKGROUND OF THE INVENTION

The estrogen receptor (ER) is a member of the nuclear hormone receptor family and functions as a ligand-activated transcription factor involved with the up and down regulation of gene expression. The natural hormone for the estrogen receptor is B17-estradiol (E2) and closely related metabolites. Binding of estradiol to the estrogen receptor causes a dimerization of the receptor and the dimer in turn binds to estrogen response elements (ERE's) on DNA. The ERDNA complex recruits other transcription factors responsible for the transcription of DNA downstream from the ERE into mRNA which is eventually translated into protein. Alternatively the interaction of ER with DNA may be indirect through the intermediacy of other transcription factors, most notably fos and jun. Since the expression of a large number of genes is regulated by the estrogen receptor and since the estrogen receptor is expressed in many cell types, modulation of the estrogen receptor through binding of either natural hormones or synthetic ER ligands can have profound effects on the physiology and pathophysiology of the organism.

A variety of diseases have their aetiology and/or pathology mediated by the ER. Collectively these diseases are called estrogen-dependent diseases. Estrogens are critical for sexual development in females. In addition, estrogens play an important role in maintaining bone density, regulation of blood lipid levels, and appear to have neuroprotective effects. Consequently decreased estrogen production in postmenopausal women is associated with a number of diseases such as osteoporosis, atherosclerosis, depression and cognitive disorders. Conversely certain types of proliferative diseases such as breast and uterine cancer and endometriosis are stimulated by estrogens and therefore antiestrogens (i.e. estrogen antagonists) have utility in the prevention and treatment of these types of disorders.

There are two different forms of the estrogen receptor, usually referred to as α and β, each encoded by a separate gene (ESR1 and ESR2, respectively).

Both ERs are widely expressed in different tissue types, however there are some notable differences in their expression patterns. The ERα is found in endometrium, breast cancer cells, ovarian stroma cells, and the hypothalamus. In males, ERα protein is found in the epithelium of the efferent ducts. The expression of the ERβ protein has been documented in kidney, brain, bone, heart, lungs, intestinal mucosa, prostate, and endothelial cells. Development therefore of selective ligands may therefore preserve the beneficial aspects of estrogen.

Breast cancer is the most common malignancy to affect women and worldwide, the incidence of the disease is increasing. Estrogens, in particular, act as endocrine growth factors for at least one-third of breast cancers, and depriving the tumour of this stimulus is a recognised therapy for advanced disease In premenopausal women, this is achieved by the ablation of ovarian function through surgical, radio-therapeutic, or medical means and, in postmenopausal women, by the use of aromatase inhibitors.

An alternative approach to estrogen withdrawal is to antagonise estrogen with antiestrogens. These are drugs that bind to and compete for estrogen receptors (ER) present in estrogen-responsive tissue. Conventional nonsteroidal anti-estrogens, such as tamoxifen, compete efficiently for ER binding but their effectiveness is often limited by the partial agonism they display, which results in an incomplete blockade of estrogen-mediated activity. A specific or "pure" antiestrogen with high affinity for ER and without any agonist effects, may have advantages over conventional nonsteroidal anti estrogens in the treatment of estrogen-dependent disease. Fulvestrant is the first of a new class of potent pure anti estrogens and is completely free of the partial agonist, estrogen-like activity, associated with currently available antiestrogens like tamoxifen.

It would be desirable to investigate other approaches to antagonise the ER receptor.

One approach would be to develop selective ER down regulators or degraders resulting in the reduction of ER expression at either the transcript or protein level.

Several methods are available for the manipulation of protein levels, including proteolysis targeting chimeric molecules (PROTACs) which contain a ligand that recognizes the target protein linked to a ligand that binds to a specific E3 ubiquitin ligase. It would be desirable to have a small molecule which can simultaneously bind ER and an E3 ubiquitin ligase and which promotes ubiquitination of ER and leads to degradation of ER by the Proteosome. One suitable E3 ubiquitin ligase is the von Hippel-Lindau tumour suppressor (VHL).

The present inventors have identified compounds which are capable of inhibiting estrogen receptor function including compounds which degrade the estrogen receptor.

SUMMARY OF THE INVENTION

In one aspect there is provided a compound of formula (I):

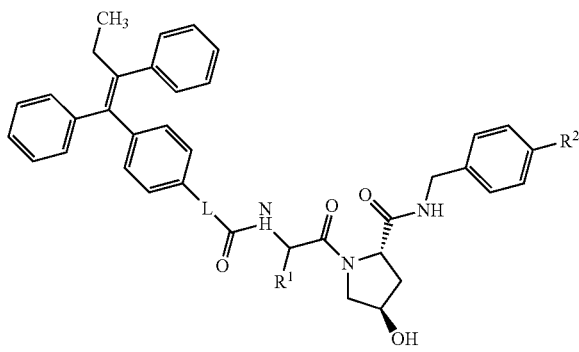

Wherein

L is a linking group comprising a length of 8-16 atoms in shortest length $R^1$ is straight or branched $C_{1-6}$alkyl, $C_{3-6}$cycloalkyl $R^2$ is 4-methylthiazol-5-yl, oxazol-5-yl, or halo or a pharmaceutically acceptable salt thereof.

In a further aspect of the present invention, there is provided a compound of formula (I), or a pharmaceutically acceptable salt thereof for use in therapy, in particular in the treatment of diseases and conditions mediated by the estrogen receptor.

In a further aspect of the present invention, there is provided a pharmaceutical composition comprising a compound of formula (I) or a pharmaceutically acceptable salt thereof and one or more of pharmaceutically acceptable carriers, diluents and excipients.

In a further aspect of the present invention, there is provided a method of treating diseases and conditions mediated by the estrogen receptor in a subject comprising administering a therapeutically effective amount of a compound of formula (I) or a pharmaceutically acceptable salt thereof.

In a further aspect of the present invention, there is provided the use of a compound of formula (I), or a pharmaceutically acceptable salt thereof in the manufacture of a medicament for use in treating diseases and conditions mediated by the estrogen receptor.

In a further aspect there is provided a combination comprising a compound of formula (I) or a pharmaceutically acceptable salt thereof and at least one further therapeutic agent.

In a further aspect there is provided a combination comprising a compound of formula (I) or a pharmaceutically acceptable salt thereof and at least one further therapeutic agent for use in therapy, particularly for treating diseases and conditions mediated by the estrogen receptor.

In a further aspect of the invention there is provided a combination comprising compound of formula (I) or a pharmaceutically acceptable salt thereof and at least one further therapeutic agent for use in treating diseases and conditions mediated by the estrogen receptor.

In a further aspect there is provided a method of treating diseases and conditions mediated by the estrogen receptor comprising administering to a human in need thereof a therapeutically effective amount of a combination comprising compound of formula (I) or a pharmaceutically acceptable salt thereof, and at least one further therapeutic agent.

In a further aspect there is provided the use of a combination comprising compound of formula (I) or a pharmaceutically acceptable salt thereof and at least one further therapeutic agent in the manufacture of a medicament for treating diseases and conditions mediated by the estrogen receptor.

In a further aspect there is provided a combination comprising a compound of formula (I) or a pharmaceutically acceptable salt thereof and at least one anti-neoplastic agent.

In a further aspect there is provided a combination comprising a compound of formula (I) or a pharmaceutically acceptable salt thereof and at least one anti-neoplastic agent, for use in therapy, in particular for diseases and conditions mediated by the estrogen receptor.

In a further aspect there is provided a combination comprising a compound of formula (I) or pharmaceutically acceptable salt thereof and at least one anti-neoplastic agent, for use in treating diseases and conditions mediated by the estrogen receptor.

In a further aspect there is provided the use of a combination comprising a compound of formula (I) or a pharmaceutically acceptable salt thereof and at least one anti-neoplastic agent, in the manufacture of a medicament for treating diseases and conditions mediated by the estrogen receptor.

In a further aspect there is provided a method of treating diseases and conditions mediated by the estrogen receptor, comprising administering to a human in need thereof a therapeutically effective amount of a combination comprising a compound of formula (I) or a pharmaceutically acceptable salt thereof and at least one anti-neoplastic agent.

In a further aspect there is provided a pharmaceutical composition comprising a combination comprising a compound of formula (I) or a pharmaceutically acceptable salt thereof and at least one further therapeutic agent, particularly at least one anti-neoplastic agent and one or more of pharmaceutically acceptable carriers, diluents and excipients.

In a further aspect there is provided a method of degrading the estrogen receptor comprising administration comprising administering to a human in need thereof a therapeutically effective amount of a compound of Formula (I) or a pharmaceutically acceptable salt thereof.

DETAILED DESCRIPTION OF THE INVENTION

As used herein, "a compound of the invention" includes all solvates, complexes, polymorphs, radiolabelled derivatives, stereoisomers and optical isomers of the compounds of formula (I) and salts thereof.

As used herein "halo" means fluoro (—F), chloro (—Cl), bromo (—Br) or iodo (—I).

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compound of formula (I) may exist in solvated and unsolvated forms. As used herein, the term "solvate" refers to a complex of variable stoichiometry formed by a solute (in this invention, a compound of formula (I) or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates.

The compounds of the invention may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

It is also noted that the compounds of formula (I) may form tautomers. It is understood that all tautomers and mixtures of tautomers of the compounds of the present invention are included within the scope of the compounds of the present invention.

As used herein, the term "estrogen receptor inhibitor", or "inhibitor" refers to any compound or treatment capable of inhibiting or reducing the expression or activity of the estrogen receptor. The inhibitor is preferably selective.

In one aspect $R^2$ is 4-methylthiazol-5-yl, oxazol-5-yl.
In one aspect $R^2$ is 4-methylthiazol-5-yl;
In one aspect the linker group is a straight chain alkylene group of 8-16 carbon atoms wherein one or more carbon atoms are replaced by a group each independently selected from
—O—, —NH—, —N(CH$_3$)—,

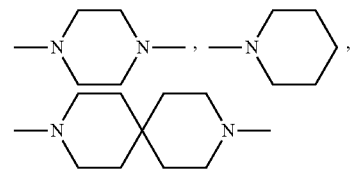

In one aspect the linker group is of formula (ii)

—(R$^3$CH$_2$CH$_2$)$_x$OCH$_2$    (ii)

Wherein each $R^3$ is independently selected from —O—, —NH—, —N(CH$_3$)— or

and x is 2-4
In one aspect at least one $R^3$ is N(CH$_3$)
In one aspect the linker is OCH$_2$CH$_2$N(CH$_3$)CH$_2$CH$_2$OCH$_2$CH$_2$OCH$_2$CHOCH$_2$ While aspects for each variable have generally been listed above separately for each variable this invention includes those compounds in which several or each aspect in formula (I) is selected from each of the aspects listed above. Therefore, this invention is intended to include all combinations of aspects for each variable.

Examples of compounds of the prevent invention include the following:

(2S,4R)-1-((S)-17-(4-((Z)-1,2-Diphenylbut-1-en-1-yl)phenoxy)-2-isopropyl-15-methyl-4-oxo-6,9,12-trioxa-3,15-diazaheptadecan-1-oyl)-4-hydroxy-N-(4-(4-methylthiazol-5-yl)benzyl)pyrrolidine-2-carboxamide

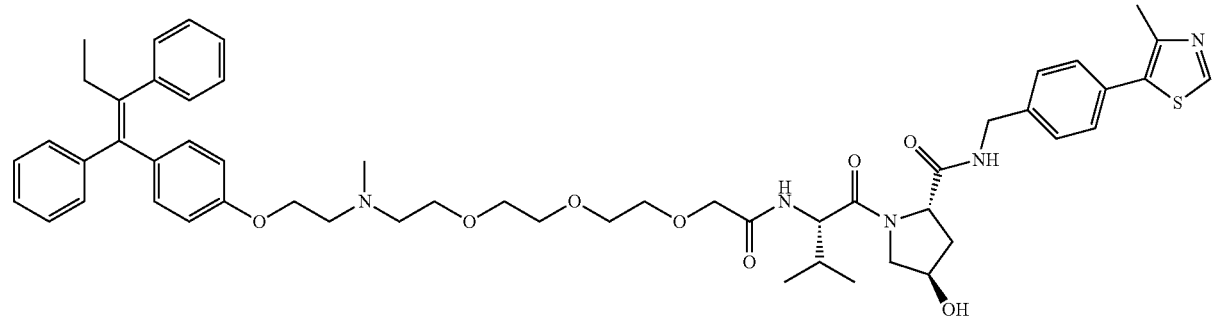 [SMILES: CC/C(=C(\c1ccccc1)c1ccc(OCCN(C)CCOCCOCCOCC(=O)N[C@H](C(=O)N2C[C@H](O)C[C@H]2C(=O)NCc2ccc(-c3scnc3C)cc2)C(C)C)cc1)c1ccccc1]

(2S,4R)-1-((S)-2-(tert-Butyl)-17-(4-((Z)-1,2-diphenylbut-1-en-1-yl)phenoxy)-15-methyl-4-oxo-6,9,12-trioxa-3,15-diazaheptadecan-1-oyl)-4-hydroxy-N-(4-(4-methylthiazol-5-yl)benzyl)pyrrolidine-2-carboxamide

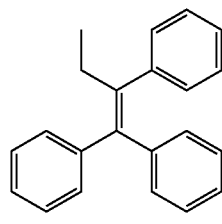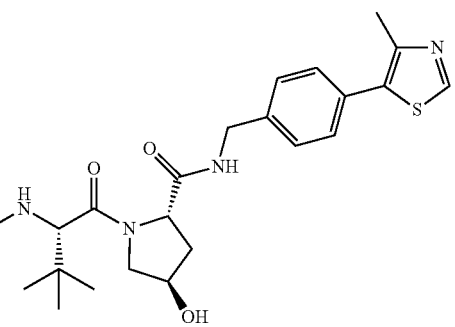

The compounds of Formula (I) may be in the form of a salt. Typically, the salts of the present invention are pharmaceutically acceptable salts. Salts encompassed within the term "pharmaceutically acceptable salts" refer to non-toxic salts of the compounds of this invention. For a review on suitable salts see Berge et al, J. Pharm. Sci. 1977, 66, 1-19.

Suitable pharmaceutically acceptable salts can include acid addition salts. A pharmaceutically acceptable acid addition salt can be formed by reaction of a compound of formula (I) with a suitable inorganic or organic acid (such as hydrobromic, hydrochloric, sulfuric, nitric, phosphoric, p-toluenesulfonic, benzenesulfonic, methanesulfonic, ethanesulfonic, naphthalenesulfonic such as 2-naphthalenesulfonic), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, p-toluenesulfonate, benzenesulfonate, methanesulfonate, ethanesulfonate, naphthalenesulfonate (e.g. 2-naphthalenesulfonate) salt.

Other non-pharmaceutically acceptable salts, e.g. trifluoroacetates, may be used, for example in the isolation of compounds of the invention, and are included within the scope of this invention.

The invention includes within its scope all possible stoichiometric and non-stoichiometric forms of the compounds of formula (I).

While it is possible that, for use in therapy, the compound of the invention may be administered as the raw chemical, it is possible to present the active ingredient as a pharmaceutical composition. Accordingly, the invention further provides pharmaceutical compositions comprising a compound of the invention and one or more pharmaceutically acceptable carriers, diluents, or excipients. The carrier(s), diluents(s) or excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable carriers, diluents or excipients. The pharmaceutical composition can be for use in the treatment and/or prophylaxis of any of the conditions described herein.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by reducing the compound to a suitable fine size and mixing with a similarly prepared pharmaceutical carrier such as an edible carbohydrate, as, for example, starch or mannitol. Flavouring, preservative, dispersing and colouring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions drops, gels or dry powders.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or in a number (such as two, three, four, five or six) of sub-doses per day such that the total daily dose is the same.

Suitably, the amount of the compound of the invention administered according to the present invention will be an amount selected from 0.01 mg to 1 g per day (calculated as the free or unsalted compound).

We have found that the compounds defined in the present invention, or a pharmaceutically acceptable salt thereof, or pharmaceutical compositions containing them, are capable of degrading the estrogen-receptor.

Accordingly, the compounds of the present invention are expected to be potentially useful agents in the treatment of diseases or medical conditions mediated alone or in part by the estrogen receptor.

Provided herein are methods of treatment or prevention of diseases, disorders and conditions mediated by the estrogen receptor. A method may comprise administering to a subject, e.g. a subject in need thereof, a therapeutically effective amount of a compound of the invention.

Thus in one aspect there is provided a compound of the invention for use in therapy Thus in one aspect there is provided a compound of the invention for use in treating diseases, disorders or conditions mediated by the estrogen receptor Thus in one aspect there is provided the use of a compound of the invention in the manufacture of a medicament for treating diseases, disorders or conditions mediated by the estrogen receptor.

In a further aspect there is provided a method of treatment of diseases, disorders or conditions mediated by the estrogen receptor in a mammal comprising administering a therapeutically effective amount of a compound of the invention.

The compound of the invention are useful in the treatment of estrogen receptor associated conditions. An "estrogen receptor-associated condition," as used herein, denotes a condition or disorder which can be treated by modulating the function or activity of an estrogen receptor in a subject, wherein treatment comprises prevention, partial alleviation or cure of the condition or disorder. Modulation may occur locally, for example, within certain tissues of the subject, or more extensively throughout a subject being treated for such a condition or disorder.

In one aspect the estrogen mediated disease or condition is breast cancer

The compounds of the present invention may be used in combination with or include one or more other therapeutic agents and may be administered either sequentially or simultaneously by any convenient route in separate or combined pharmaceutical compositions. The therapeutically effective amount of the further therapeutic agents of the present invention will depend upon a number of factors including, for example, the age and weight of the mammal, the precise condition requiring treatment, the severity of the condition, the nature of the formulation, and the route of administration. Ultimately, the therapeutically effective amount will be at the discretion of the attendant physician or veterinarian. The relative timings of administration will be selected in order to achieve the desired combined therapeutic effect.

The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and vice versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of formula (I) is used in combination with a second therapeutic agent active against the same disease, condition or disorder, the dose of each compound may differ from that when the compound is used alone. Appropriate doses will be readily appreciated by those skilled in the art.

In one embodiment, the compound of compound of formula (I) or a pharmaceutically acceptable salt thereof may be employed with other therapeutic methods of cancer treatment. In particular, in anti-neoplastic therapy, combination therapy with other chemotherapeutic, hormonal, antibody agents as well as surgical and/or radiation treatments other than those mentioned above are envisaged.

In one embodiment, the further anti-cancer therapy is surgical and/or radiotherapy.

In one embodiment, the further anti-cancer therapy is at least one additional anti-neoplastic agent.

Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; and cell cycle signaling inhibitors.

Anti-Microtubule or Anti-Mitotic Agents:

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β, 10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum Coordination Complexes:

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma.

Alkylating Agents:

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]-benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic Anti-Neoplastics:

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II Inhibitors:

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite Neoplastic Agents:

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl)methyl] methylamino]benzoyl]L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Topoisomerase I Inhibitors:

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and Hormonal Analogues:

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, estrogens, and anti-estrogens such as fulvestrant, flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal Transduction Pathway Inhibitors:

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-Angiogenic Agents:

(i) Anti-angiogenic agents including non-receptor MEK angiogenesis inhibitors may also be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin);

Immunotherapeutic Agents:

Agents used in immunotherapeutic regimens may also be useful in combination with the compounds of formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies Proapoptotic Agents:

Agents used in proapoptotic regimens (e.g., bcl-2 antisense oligonucleotides) may also be used in the combination of the present invention.

Cell Cycle Signalling Inhibitors

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a compound of formula I or a salt or solvate thereof and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEK angiogenesis inhibitors, immunotherapeutic agents, proapoptotic agents, and cell cycle signaling inhibitors.

In one embodiment, the combination of the present invention comprises a compound of formula I or a salt or solvate thereof and at least one anti-neoplastic agent which is an anti-microtubule agent selected from diterpenoids and vinca alkaloids.

In a further embodiment, at least one anti-neoplastic agent agent is a diterpenoid.

In a further embodiment, at least one anti-neoplastic agent is a vinca alkaloid.

In one embodiment, the combination of the present invention comprises a compound of formula I or a salt or solvate thereof and at least one anti-neoplastic agent, which is a platinum coordination complex.

In a further embodiment, at least one anti-neoplastic agent is paclitaxel, carboplatin, or vinorelbine.

In a further embodiment, at least one anti-neoplastic agent is carboplatin.

In a further embodiment, at least one anti-neoplastic agent is vinorelbine.

In a further embodiment, at least one anti-neoplastic agent is paclitaxel.

In one embodiment, the combination of the present invention comprises a compound of formula I and salts or solvates thereof and at least one anti-neoplastic agent which is a signal transduction pathway inhibitor.

In a further embodiment the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms.

In a further embodiment the signal transduction pathway inhibitor is an inhibitor of a serine/threonine kinase rafk, akt, or PKC-zeta.

In a further embodiment the signal transduction pathway inhibitor is an inhibitor of a non-receptor tyrosine kinase selected from the src family of kinases.

In a further embodiment the signal transduction pathway inhibitor is an inhibitor of c-src.

In a further embodiment the signal transduction pathway inhibitor is an inhibitor of Ras oncogene selected from inhibitors of farnesyl transferase and geranylgeranyl transferase.

In a further embodiment the signal transduction pathway inhibitor is an inhibitor of a serine/threonine kinase selected from the group consisting of PI3K.

In a further embodiment the signal transduction pathway inhibitor is a dual EGFr/erbB2 inhibitor, for example N-{3-Chloro-4-[(3-fluorobenzyl)oxy]phenyl}-6-[5-({[2-(methanesulphonyl)ethyl]amino}methyl)-2-furyl]-4-quinazolinamine (structure below):

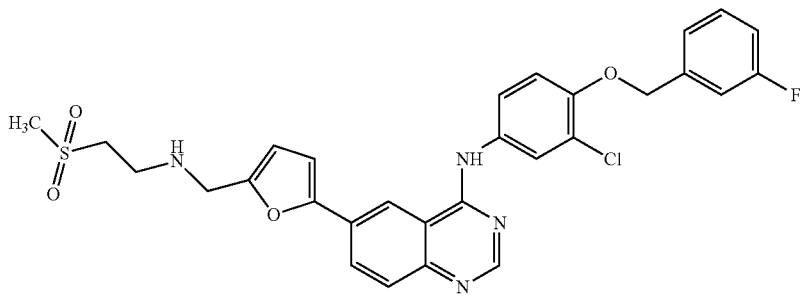 [SMILES: CS(=O)(=O)CCNCc1ccc(-c2ccc3ncnc(Nc4ccc(OCc5cccc(F)c5)c(Cl)c4)c3c2)o1]

In one embodiment, the combination of the present invention comprises a compound of formula I or a salt or solvate thereof and at least one anti-neoplastic agent which is a cell cycle signaling inhibitor.

In further embodiment, cell cycle signaling inhibitor is an inhibitor of CDK2, CDK4 or CDK6.

Particular components of combination therapy include combinations with other anti-estrogens including tamoxifen and/or fulvestrant.

In one embodiment the mammal in the methods and uses of the present invention is a human.

General Synthetic Methods

Compounds of general formula (I) may be prepared by methods known in the art of organic synthesis as set forth in the specific Examples described below. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

Experimental
Abbreviations:
DCM: dichloromethane.
DIPEA: N,N-diisopropylethylamine.
DMF: N,N-dimethylformamide.
h: hour.
HATU: 2-(7-aza-1H-benzotriazole-1-yl)-1,1,3,3-tetramethyluronium hexafluorophosphate.
HPLC: high-performance liquid chromatography.
LCMS: liquid chromatography-mass spectrometry
Min: minutes.
NMR: Nuclear magnetic resonance.
RT: retention time.
tBu: tert-butoxide.
TFA: trifluoroacetic acid.
THF: tetrahydrofuran.

LCMS Method A:

The analysis was conducted on an Acquity UPLC BEH C18 column (50 mm×2.1 mm internal diameter 1.7 µm packing diameter) at 40° C.

The solvents employed were:
A=0.1% v/v solution of formic acid in water.
B=0.1% v/v solution of formic acid in acetonitrile.

The gradient employed was as follows:

| Time (minutes) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

LCMS Method B:

The analysis was conducted on an Acquity UPLC BEH C18 column (50 mm×2.1 mm internal diameter 1.7 µm packing diameter) at 40° C.

The solvents employed were:
A=10 mM ammonium bicarbonate in water adjusted to pH 10 with ammonia solution.
B=acetonitrile.

The gradient employed was as follows:

| Time (minutes) | Flow Rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 99 | 1 |

The UV detection was an averaged signal from wavelength of 210 nm to 350 nm and mass spectra were recorded on a mass spectrometer using alternate-scan positive and negative mode electrospray ionization.

The following illustrates the mobile phases and gradients used when compounds underwent purification by mass-directed autopreparative HPLC.

Mass-Directed Autopreparative HPLC (Formic Acid Modifier)

The HPLC analysis was conducted on a Sunfire C18 column (150 mm×30 mm internal diameter, 5 µm packing diameter) at ambient temperature.

The solvents employed were:
A=0.1% v/v solution of formic acid in water.
B=0.1% v/v solution of formic acid in acetonitrile.

Mass-Directed Autopreparative HPLC (Trifluoroacetic Acid Modifier)

The HPLC analysis was conducted on a Sunfire C18 column (150 mm×30 mm internal diameter, 5 µm packing diameter) at ambient temperature.

The solvents employed were:
A=0.1% v/v solution of trifluoroacetic acid in water.
B=0.1% v/v solution of trifluoroacetic acid in acetonitrile.

Mass-Directed Autopreparative HPLC (Ammonium Bicarbonate Modifier)

The HPLC analysis was conducted on an XBridge C18 column (150 mm×30 mm internal diameter, 5 µm packing diameter) at ambient temperature.

The solvents employed were:
A=10 mM ammonium bicarbonate in water adjusted to pH 10 with ammonia solution.
B=acetonitrile.

For each of the mass-directed autopreparative purifications, irrespective of the modifier used, the gradient employed was dependent upon the retention time of the particular compound undergoing purification as recorded in the analytical LCMS, and was as follows:

For compounds with an analytical LCMS retention time below 0.6 minutes the following gradient was used:

| Time (minutes) | Flow Rate (mL/min) | % A | % B |
| --- | --- | --- | --- |
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
| --- | --- | --- | --- |
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
| --- | --- | --- | --- |
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
| --- | --- | --- | --- |
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

For compounds with an analytical LCMS retention time greater than 1.4 minutes (LCMS method A) or greater than 3.6 minutes (LCMS method B) the following gradient was used:

| Time (minutes) | Flow Rate (mL/min) | % A | % B |
| --- | --- | --- | --- |
| 0 | 40 | 20 | 80 |
| 1 | 40 | 20 | 80 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

The chemical names were generated using ACD Name Pro version 6.02 from Advanced Chemistry Development, Inc.

(Z)-2-(4-(1,2-Diphenylbut-1-en-1-yl)phenoxy)-N-methylethanamine can be prepared according to the process described by Dreaden, Erik C. et al. *Bioconjugate Chem.* 2009, 20, 2247-2253.

tert-Butyl 1-phenyl-2,5,8,11-tetraoxatridecan-13-oate

Potassium tert-butoxide (commercially available from for example Aldrich) (7.71 g, 68.7 mmol) was added to a stirred solution of 2-(2-(2-(benzyloxy)ethoxy)ethoxy)ethanol (commercially available from for example Fluorochem) (15 g, 62.4 mmol) in tert-butanol (200 mL) and the reaction mixture was stirred at room temperature for 2 h. The reaction mixture was cooled to 0° C., tert-butyl 2-bromoacetate (commercially available from for example Aldrich) (16.59 mL, 112 mmol) was added, and the mixture was stirred at room temperature overnight. DCM (300 mL) was added ant the organic phase was washed with water (300 mL) and then brine (2×200 mL). The organic extract was dried using a hydrophobic frit and concentrated under reduced pressure to give the crude product as a yellow oil. The product was purified by chromatography on silica using a gradient elution from 0% to 100% methyl tert-butyl ether in cyclohexane to afford the title compound (13.3 g, 37.5 mmol, 60% yield). LCMS (Method A) RT=1.10 min, ES+ve m/z 372.4 $[M+NH_4]^+$.

tert-Butyl 2-(2-(2-(2-hydroxyethoxy)ethoxy)ethoxy) acetate

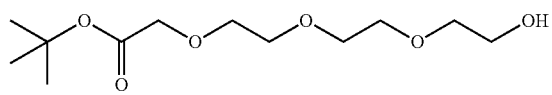 [SMILES: CC(C)(C)OC(=O)COCCOCCOCCO]

A mixture of tert-butyl 1-phenyl-2,5,8,11-tetraoxatridecan-13-oate (13.3 g, 37.5 mmol) and palladium on carbon (10% w/w, 11.38 g, 10.69 mmol) in ethanol (200 mL) was stirred at room temperature under an atmosphere of hydrogen for 1.5 h. The palladium on carbon was filtered through celite and the filtrate was evaporated under reduced pressure to afford the title compound (9.74 g, 36.8 mmol, 98% yield) as a yellow oil. $^1$H NMR (400 MHz, DMSO-d6) δ=4.54 (s, 1H), 3.99 (s, 2H), 3.60-3.40 (m, 12H), 1.43 (s, 9H).

tert-Butyl 2-(2-(2-(2-(tosyloxy)ethoxy)ethoxy) ethoxy)acetate

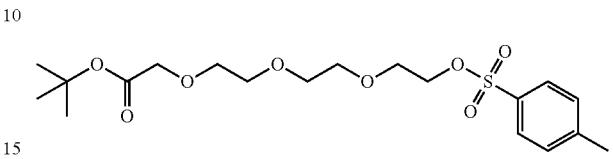

Tosylchloride (commercially available from for example Aldrich) (11.94 g, 62.6 mmol) was added to a cooled solution (0° C.) of tert-butyl 2-(2-(2-(2-hydroxyethoxy) ethoxy)ethoxy)acetate (9.74 g, 36.8 mmol) in pyridine (150 mL). The reaction was stirred at room temperature for 16 h. The reaction mixture was partitioned between ethyl acetate (300 mL) and aqueous HCl (2M, 300 mL). The organic extract was washed with further aqueous HCl (2M, 300 mL), saturated $K_2CO_3$ (100 mL) and brine (100 mL). The organic extract was dried using $MgSO_4$ and concentrated under reduced pressure to afford the title compound (10.3 g, 24.6 mmol, 67% yield) as a yellow oil. LCMS (Method A) RT=1.14 min, ES+ve 436.2 $[M+NH_4]^+$.

(Z)-tert-Butyl 1-(4-(1,2-diphenylbut-1-en-1-yl)phenoxy)-3-methyl-6,9,12-trioxa-3-azatetradecan-14-oate

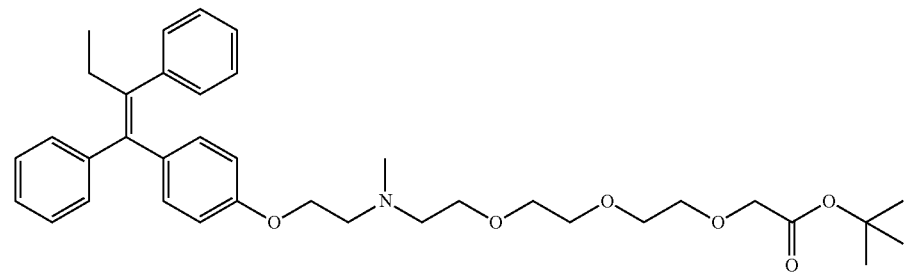 [SMILES: CC/C(=C(\c1ccccc1)c1ccc(OCCN(C)CCOCCOCCOCC(=O)OC(C)(C)C)cc1)c1ccccc1]

A mixture of (Z)-2-(4-(1,2-diphenylbut-1-en-1-yl)phenoxy)-N-methylethanamine (141 mg, 0.394 mmol), tert-butyl 2-(2-(2-(2-(tosyloxy)ethoxy)ethoxy)ethoxy)acetate (0.187 mL, 0.592 mmol) and $K_2CO_3$ (545 mg, 3.94 mmol) in DMF (5 mL) was heated at 85° C. for 16 h. The reaction was cooled to room temperature and partitioned between EtOAc (30 mL) and water (30 mL). The organic extract was dried using a hydrophobic frit and concentrated under reduced pressure. The product was purified by chromatography on silica using a gradient elution from 0% to 100% EtOAc in cyclohexane followed by a 0% to 25% methanol in dichloromethane to afford the title compound (141 mg, 0.234 mmol, 59% yield) as a colourless glass. LCMS (Method B) RT=1.63 min, ES+ve m/z 604.2 $[M+H]^+$.

(Z)-1-(4-(1,2-Diphenylbut-1-en-1-yl)phenoxy)-3-methyl-6,9,12-trioxa-3-azatetradecan-14-oic acid

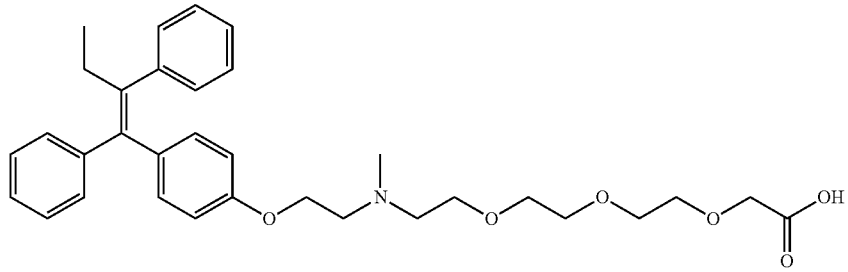 [SMILES: CC/C(=C(\c1ccccc1)c1ccc(OCCN(C)CCOCCOCCOCC(=O)O)cc1)c1ccccc1]

A mixture of (Z)-tert-butyl 1-(4-(1,2-diphenylbut-1-en-1-yl)phenoxy)-3-methyl-6,9,12-trioxa-3-azatetradecan-14-oate (141 mg, 0.234 mmol), and TFA (1 mL, 12.98 mmol) in DCM (1 mL) was stirred at room temperature for 1.5 h. The reaction mixture was evaporated under reduced pressure and the residue was then subjected to purification by mass-directed automated preparative HPLC (ammonium carbonate modifier) to afford the title compound (81 mg, 0.148 mmol, 63% yield) as a colourless glass. LCMS (Method B) RT=1.14 min, ES+ve m/z 548.2 [M+H]$^+$.

(2S,4R)-tert-Butyl 2-((4-bromobenzyl)carbamoyl)-4-hydroxypyrrolidine-1-carboxylate

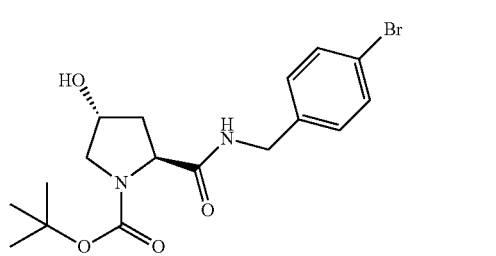 [SMILES: CC(C)(C)OC(=O)N1C[C@H](O)C[C@H]1C(=O)NCc1ccc(Br)cc1]

An ice-cooled mixture of (2S,4R)-1-(tert-butoxycarbonyl)-4-hydroxypyrrolidine-2-carboxylic acid (commercially available from for example Aldrich) (7.95 g, 34.4 mmol) and (4-bromophenyl)methanamine (commercially available from for example FluroChem) (6.4 g, 34.4 mmol) in DMF (200 mL) was treated with DIPEA (18.02 mL, 103 mmol) and then with HATU (14.39 g, 37.8 mmol) and the mixture was stirred at ambient temperature for 30 minutes. The reaction was quenched with water (200 mL) and extracted with ethyl acetate (2×200 mL). The combined organic layers were washed with saturated aqueous sodium bicarbonate (2×300 mL), water (100 mL), brine (200 mL), dried over magnesium sulphate and evaporated to dryness. The product was purified by chromatography on silica using a gradient elution from 0% to 10% methanol in DCM to afford the title compound (12.9 g, 32.3 mmol, 94% yield). LCMS (Method A) RT=0.87 min, ES+ve m/z 399.2/401.2 [M+H]$^+$.

(2S,4R)-tert-butyl 4-hydroxy-2-((4-(4-methylthiazol-5-yl)benzyl)carbamoyl)pyrrolidine-1-carboxylate

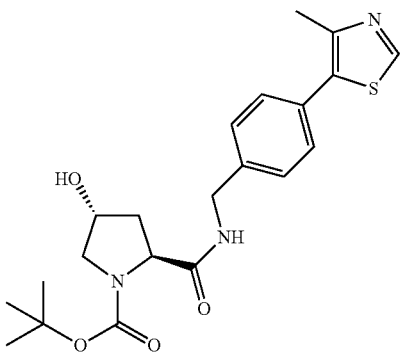 [SMILES: Cc1ncsc1-c1ccc(CNC(=O)[C@@H]2C[C@@H](O)CN2C(=O)OC(C)(C)C)cc1]

A mixture of (2S,4R)-tert-butyl 2-((4-bromobenzyl)carbamoyl)-4-hydroxypyrrolidine-1-carboxylate (12.9 g, 32.3 mmol), 4-methylthiazole (commercially available from for example Aldrich) (5.88 mL, 64.6 mmol), palladium(II) acetate (commercially available from for example Aldrich) (0.145 g, 0.646 mmol) and potassium acetate (6.34 g, 64.6 mmol) in N-methyl-2-pyrrolidone (80 mL) was stirred at 120° C. under nitrogen for 18 hours. Water (100 ml) was added and the product was extracted with ethyl acetate (4×300 mL). The combined organic phase was washed with brine (5×200 mL), dried over magnesium sulfate and evaporated to dryness. The product was purified by chromatography on silica using a gradient elution from 0% to 10% methanol in DCM to afford the title compound (8 g, 19.2 mmol, 59% yield). LCMS (Method A) RT=0.75 min, ES+ve m/z 418.4 [M+H]$^+$.

29

(2S,4R)-4-Hydroxy-N-(4-(4-methylthiazol-5-yl)benzyl)pyrrolidine-2-carboxamide, hydrochloride

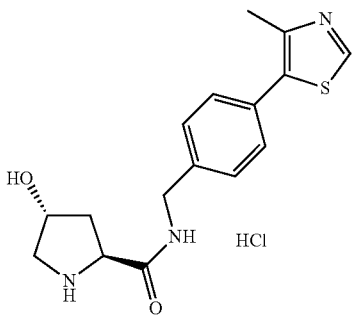 [SMILES: Cc1ncsc1-c1ccc(CNC(=O)[C@@H]2C[C@@H](O)CN2)cc1 ; Cl]

(2S,4R)-tert-Butyl 4-hydroxy-2-((4-(4-methylthiazol-5-yl)benzyl)carbamoyl)pyrrolidine-1-carboxylate (8 g, 19.16 mmol) was dissolved in methanol (30 mL) and DCM (20 mL) and treated with HCl in dioxane (4M, 8.08 mL, 32.3 mmol). The reaction mixture was stirred at ambient temperature for 2 hours. The solvent was removed under reduced pressure and the residue was triturated with DCM, filtered and dried under reduced pressure to afford the title compound (6.7 g, 18.9 mmol, 99% yield). LCMS (Method A) RT=0.49 min, ES+ve m/z 318.3 [M+H]+.

tert-Butyl ((S)-1-((2S,4R)-4-hydroxy-2-((4-(4-methylthiazol-5-yl)benzyl)carbamoyl)pyrrolidin-1-yl)-3-methyl-1-oxobutan-2-yl)carbamate

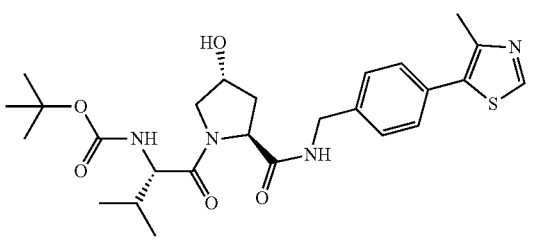 [SMILES: Cc1ncsc1-c1ccc(CNC(=O)[C@@H]2C[C@@H](O)CN2C(=O)[C@@H](NC(=O)OC(C)(C)C)C(C)C)cc1]

A stirred mixture of (2S,4R)-4-hydroxy-N-(4-(4-methylthiazol-5-yl)benzyl)pyrrolidine-2-carboxamide, hydrochloride (125 mg, 0.35 mmol) and (S)-2-((tert-butoxycarbonyl)amino)-3-methylbutanoic acid (commercially available from for example Aldrich) (77 mg, 0.35 mmol) in DMF (0.9 mL) was treated with DIPEA (0.22 mL, 1.3 mmol) and then with HATU (134 mg, 0.35 mmol) and the mixture was stirred at ambient temperature for 1 hour. The reaction mixture was subjected directly to purification by mass-directed automated preparative HPLC (formic acid modifier) to afford the title compound (120 mg, 0.232 mmol, 72% yield). LCMS (Method A) RT=0.87 min, ES+ve m/z 517.3 [M+H]+.

30

(2S,4R)-1-((S)-2-Amino-3-methylbutanoyl)-4-hydroxy-N-(4-(4-methylthiazol-5-yl)benzyl)pyrrolidine-2-carboxamide, hydrochloride

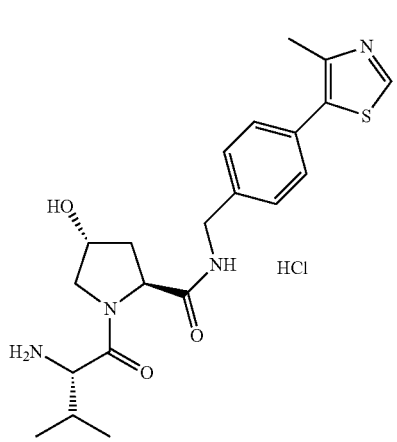 [SMILES: Cc1ncsc1-c1ccc(CNC(=O)[C@@H]2C[C@@H](O)CN2C(=O)[C@@H](N)C(C)C)cc1 ; Cl]

A solution of tert-butyl ((S)-1-((2S,4R)-4-hydroxy-2-((4-(4-methylthiazol-5-yl)benzyl)carbamoyl)pyrrolidin-1-yl)-3-methyl-1-oxobutan-2-yl)carbamate (287 mg, 0.56 mmol) in THF (5 mL) was treated with HCl in 1,4-dioxan (4M, 10 mL, 40 mmol) and stirred at ambient temperature for 2 hours. The mixture was evaporated to dryness to afford the title compound (224 mg, 0.49 mmol, quantitative). LCMS (Method A) RT=0.55 min, ES+ve m/z 417.3 [M+H]+.

(2S,4R)-1-((S)-2-Amino-3,3-dimethylbutanoyl)-4-hydroxy-N-(4-(4-methylthiazol-5-yl)benzyl)pyrrolidine-2-carboxamide, hydrochloride A stirred mixture of (2S,4R)-4-hydroxy-N-(4-(4-methylthiazol-5-yl)benzyl)pyrrolidine-2-carboxamide, hydrochloride (70 mg, 0.20 mmol) and (S)-2-((tert-butoxycarbonyl)amino)-3,3-dimethylbutanoic acid (commercially available from for example Fluka) (50 mg, 0.22 mmol) in DMF (1 mL) was treated with DIPEA (0.14 mL, 0.79 mmol) and then with HATU (90 mg, 0.24 mmol), and stirred at ambient temperature for 30 minutes. The reaction mixture was subjected directly to purification by mass-directed automated preparative HPLC (formic acid modifier) to give the intermediate boc-protected product. The intermediate was then dissolved in a mixture of dichloromethane (0.5 mL) and methanol (0.1 mL) and treated with HCl in 1,4-dioxane (4M, 0.25 mL, 1.0 mmol). After stirring at ambient temperature for 1 hour, the reaction mixture was evaporated to dryness and the residue triturated to a solid with dichloromethane and dried under vacuum to afford the title compound (76 mg, 0.163 mmol, 82% yield). LCMS (Method A) RT=0.58 min, ES+ve m/z 431.2 [M+H]⁺.

Example 1

(2S,4R)-1-((S)-17-(4-((Z)-1,2-Diphenylbut-1-en-1-yl)phenoxy)-2-isopropyl-15-methyl-4-oxo-6,9,12-trioxa-3,15-diazaheptadecan-1-oyl)-4-hydroxy-N-(4-(4-methylthiazol-5-yl)benzyl)pyrrolidine-2-carboxamide N26699-42

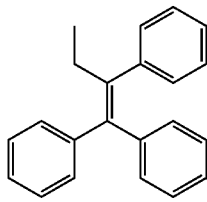
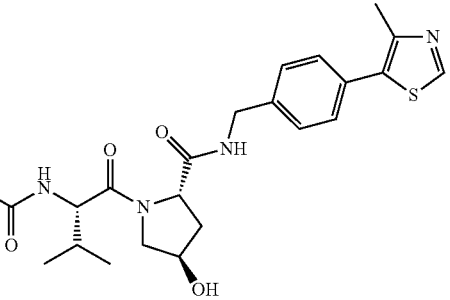

HATU (26 mg, 0.068 mmol) was added to a mixture of (2S,4R)-1-((S)-2-amino-3-methylbutanoyl)-4-hydroxy-N-(4-(4-methylthiazol-5-yl)benzyl)pyrrolidine-2-carboxamide, hydrochloride, (25 mg, 0.055 mmol), (Z)-1-(4-(1,2-diphenylbut-1-en-1-yl)phenoxy)-3-methyl-6,9,12-trioxa-3-azatetradecan-14-oic acid (27 mg, 0.049 mmol) and DIPEA (0.05 mL, 0.286 mmol) in DMF (0.8 mL). The reaction was stirred at room temperature for 10 minutes. The solution was directly subjected to purification by mass-directed automated preparative HPLC (ammonium carbonate modifier) to afford the title compound (36 mg, 0.038 mmol, 77% yield). LCMS (Method B) RT=1.44 min, ES+ve m/z 946.2 [M+H]⁺.

Example 2

(2S,4R)-1-((S)-2-(tert-Butyl)-17-(4-((Z)-1,2-diphenylbut-1-en-1-yl)phenoxy)-15-methyl-4-oxo-6,9,12-trioxa-3,15-diazaheptadecan-1-oyl)-4-hydroxy-N-(4-(4-methylthiazol-5-yl)benzyl)pyrrolidine-2-carboxamide N26699-42

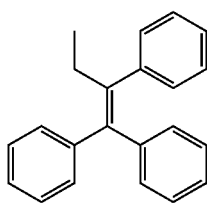
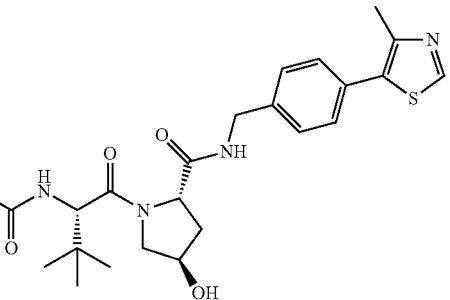

HATU (26 mg, 0.068 mmol) was added to a mixture of (2S,4R)-1-((S)-2-amino-3,3-dimethylbutanoyl)-4-hydroxy-N-(4-(4-methylthiazol-5-yl)benzyl)pyrrolidine-2-carbox-amide, hydrochloride (25 mg, 0.054 mmol), (Z)-1-(4-(1,2-diphenylbut-1-en-1-yl)phenoxy)-3-methyl-6,9,12-trioxa-3-azatetradecan-14-oic acid (27 mg, 0.049 mmol) and DIPEA (0.05 mL, 0.286 mmol) in DMF (0.8 mL). The reaction was stirred at room temperature for 10 minutes. The solution was directly subjected to purification by mass-directed automated preparative HPLC (ammonium carbonate modifier) to afford the title compound (14 mg, 0.014 mmol, 30% yield). LCMS (Method B) RT=1.48 min, ES+ve m/z 960.2 [M+H]⁺.

Estrogen Receptor Alpha (ERa) Degradation and Cell Count Imaging Assay

Compounds were assessed for ERa degradation and cell count effects in an MCF-7 cell line using high content imaging. 50 µl of MCF-7 cell suspension in media was dispensed to each well of black walled, clear bottomed, PDL-coated plates, containing a defined concentration of test compound dissolved in DMSO covering concentration range from 0.03 uM to 30 uM. Cells were incubated in the presence of compound for 24 hours at 37° C., 5% CO₂ before cells were fixed. After incubation with the fixative solution (4% formaldehyde) the wells were aspirated and a solution containing detergent was added to permeabilise the cells followed by addition of blocking solution containing 1% BSA (bovine serum albumin) to block the non-specific binding sites. After a further incubation for 1 hour this solution was aspirated from the wells and the ERa specific antibody diluted in blocking solution at concentration 1 ug/ml (anti ERα, cat no sc-543, Santa Cruz) was added. Following incubation with the antibody for 2 hours the cells were washed with a PBS-based solution before addition of a secondary anti rabbit fluorescently-labelled Alexa Fluor 488 goat antibody at 2 ug/ml concentration (cat no11008, Invitrogen) and a nuclear staining dye Hoechst33342 at 1 ug/ml concentration (cat no H3570, invitrogen). Following a further incubation for 1 hour the cells were again washed with the PBS-based solution. The plates were then imaged and the intensity of ERa staining in the nucleus and cell count measured. ERa degradation activity was expressed relative to DMSO, giving 0% degradation, and an in-house degrader molecule classified as giving 100% activity. Cell count reduction was expressed relative to DMSO, classified as 0% reduction.

Examples showed evidence of ERa degradation in this assay relative to the DMSO control at 1 uM concentration.

What is claimed is:

1. A compound of formula (I):

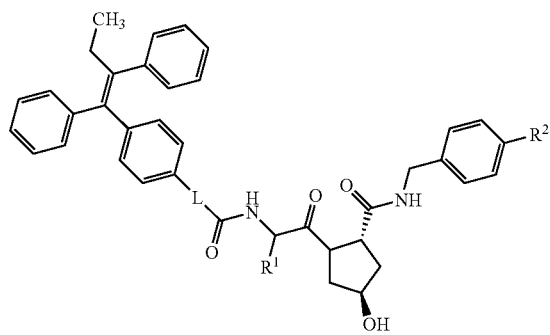

herein
L is an alkylene linking group of 5-16 carbon atoms;
$R^1$ is straight or branched $C_{1-6}$alkyl, $C_{3-6}$ cycloalkyl;
$R^2$ is 4-methylthiazol-5-yl, oxazol-5-yl, halogen
or a pharmaceutically acceptable salt thereof.

2. A compound or a pharmaceutically acceptable salt thereof according to claim 1 wherein $R^2$ is 4-methylthiazol-5-yl, oxazol-5-yl.

3. A compound or a pharmaceutically acceptable salt thereof according to claim 2 wherein $R^2$ is 4-methylthiazol-5-yl.

4. The compound or a pharmaceutically acceptable salt thereof according to claim 1, wherein one or more carbon atoms of the linking group (L) are replaced by a member of the group independently selected from a heteroatom, —O—, —NH—, —N(CH₃)—,

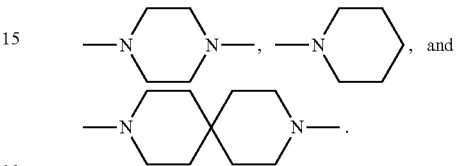

5. A compound or a pharmaceutically acceptable salt thereof according to claim 1 wherein the linker group is of formula (ii)

$$—(R^3CH_2CH_2)_xOCH_2—$$ (ii)

wherein each $R^3$ is independently —O—, —NH—, —N(CH₃)— or

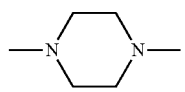

and x is 2-4.

6. A compound or a pharmaceutically acceptable salt thereof according to claim 5 wherein at least one $R^3$ is N(CH₃).

7. A compound or a pharmaceutically acceptable salt thereof according to claim 1 wherein the linker is OCH₂CH₂N(CH₃)CH₂CH₂OCH₂CH₂OCH₂CHOCH₂.

8. A compound of formula (I) according to claim 1 which is selected from the group consisting of (2S,4R)-1-((S)-17-(4-((Z)-1,2-Diphenylbut-1-en-1-yl)phenoxy)-2-isopropyl-15-methyl-4-oxo-6,9,12-trioxa-3,15-diazaheptadecan-1-oyl)-4-hydroxy-N-(4-(4-methylthiazol-5-yl)benzyl)pyrrolidine-2-carboxamide

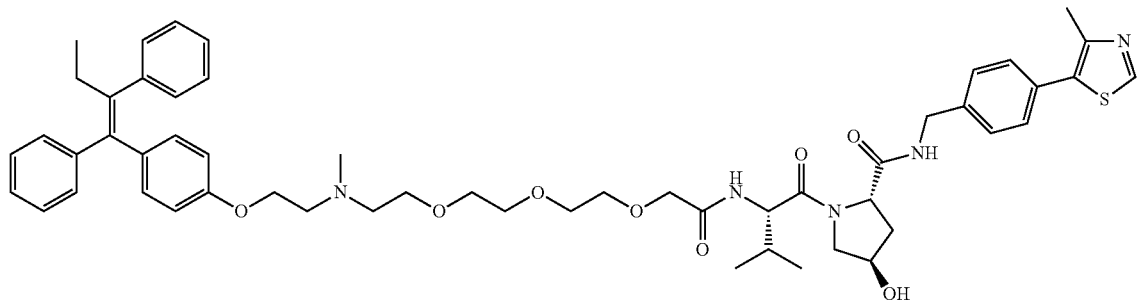 [SMILES: CC/C(=C(\c1ccccc1)c1ccc(OCCN(C)CCOCCOCCOCC(=O)N[C@H](C(=O)N2C[C@H](O)C[C@H]2C(=O)NCc2ccc(-c3scnc3C)cc2)C(C)C)cc1)c1ccccc1]

(2S,4R)-1-((S)-2-(tert-Butyl)-17-(4-((Z)-1,2-diphenyl-but-1-en-1-yl)phenoxy)-15-methyl-4-oxo-6,9,12-tri-oxa-3,15-diazaheptadecan-1-oyl)-4-hydroxy-N-(4-(4-methylthiazol-5-yl)benzyl)pyrrolidine-2-carboxamide

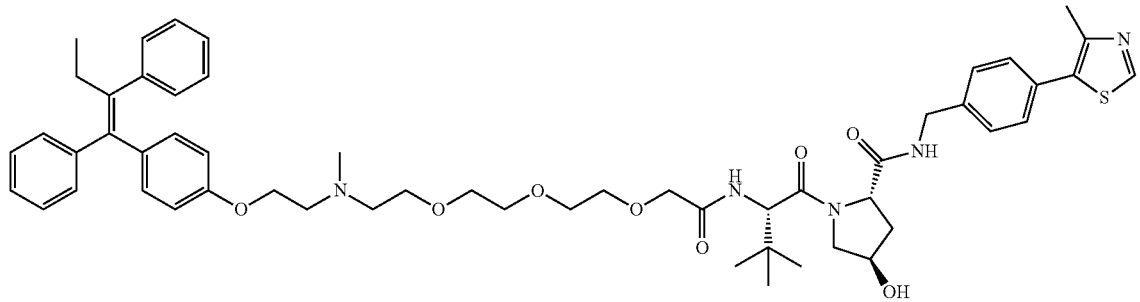 [SMILES: CC/C(=C(\c1ccccc1)c1ccc(OCCN(C)CCOCCOCCOCC(=O)N[C@H](C(=O)N2C[C@H](O)C[C@H]2C(=O)NCc2ccc(-c3scnc3C)cc2)C(C)(C)C)cc1)c1ccccc1]

and pharmaceutically acceptable salts thereof.

9. A pharmaceutical composition comprising a compound of claim 1 or a pharmaceutically acceptable salt thereof and one or more of pharmaceutically acceptable carriers, diluents and excipients.

10. A combination comprising a compound of claim 1 or a pharmaceutically acceptable salt thereof, and at least one anti-neoplastic agent.

11. A pharmaceutical composition comprising a compound of claim 1 or a pharmaceutically acceptable salt thereof and at least one anti-neoplastic agent and one or more of pharmaceutically acceptable carriers, diluents and excipients.

12. A method of degrading estrogen receptor protein comprising administering to a cell a therapeutically effective amount of a compound of claim 1 or a pharmaceutically acceptable salt thereof, wherein the compound is effective for degrading the estrogen receptor protein.

* * * * *